(12) United States Patent
Hall et al.

(10) Patent No.: US 9,198,999 B2
(45) Date of Patent: Dec. 1, 2015

(54) DRUG-ELUTING ROTATIONAL SPUN COATINGS AND METHODS OF USE

(71) Applicant: Merit Medical Systems, Inc., South Jordan, UT (US)

(72) Inventors: John William Hall, North Salt Lake, UT (US); Rachel L. Simmons, Bountiful, UT (US); Aaron Hopkinson, Herriman, UT (US); Bart Dolmatch, Dallas, TX (US); Zeke Eller, Dallas, TX (US); Robert S. Kellar, Flagstaff, AZ (US)

(73) Assignee: Merit Medical Systems, Inc., South Jordan, UT (US)

( * ) Notice: Subject to any disclaimer, the term of this patent is extended or adjusted under 35 U.S.C. 154(b) by 28 days.

(21) Appl. No.: 13/787,327

(22) Filed: Mar. 6, 2013

(65) Prior Publication Data
US 2014/0086971 A1    Mar. 27, 2014

Related U.S. Application Data

(60) Provisional application No. 61/704,212, filed on Sep. 21, 2012.

(51) Int. Cl.
| | |
|---|---|
| *A61L 27/34* | (2006.01) |
| *A61L 27/54* | (2006.01) |
| *A61L 27/28* | (2006.01) |
| *A61L 29/08* | (2006.01) |
| *A61L 29/18* | (2006.01) |
| *A61L 31/10* | (2006.01) |
| *A61L 31/16* | (2006.01) |
| *A61L 29/16* | (2006.01) |

(52) U.S. Cl.
CPC ............ *A61L 27/34* (2013.01); *A61L 27/28* (2013.01); *A61L 27/54* (2013.01); *A61L 29/085* (2013.01); *A61L 29/16* (2013.01); *A61L 31/10* (2013.01); *A61L 31/16* (2013.01); *A61L 2300/416* (2013.01); *A61L 2420/08* (2013.01)

(58) Field of Classification Search
None
See application file for complete search history.

(56) References Cited

U.S. PATENT DOCUMENTS

| | | | |
|---|---|---|---|
| 4,043,331 | A | 8/1977 | Martin et al. |
| 4,044,404 | A | 8/1977 | Martin et al. |
| 4,096,227 | A | 6/1978 | Gore |
| 4,127,706 | A | 11/1978 | Martin et al. |
| 4,323,525 | A | 4/1982 | Bornat |

(Continued)

FOREIGN PATENT DOCUMENTS

| | | |
|---|---|---|
| EP | 0457456 | 11/1991 |
| EP | 2363516 | 9/2011 |

(Continued)

OTHER PUBLICATIONS

Restriction Requirement dated Jun. 21, 2013 for U.S. Appl. No. 13/360,444.

(Continued)

*Primary Examiner* — Carlos Azpuru
*Assistant Examiner* — Casey Hagopian
(74) *Attorney, Agent, or Firm* — Stoel Rives LLP

(57) ABSTRACT

Drug-eluting rotational spun coatings that include one or more therapeutic agents may be used to coat a medical device. The medical devices include, for example, balloon catheters, vascular grafts and stents, which are coated with drug-eluting rotational spun materials that may be used to deliver a therapeutic agent to a target tissue or body lumen.

33 Claims, 20 Drawing Sheets

(56) References Cited

U.S. PATENT DOCUMENTS

| | | | |
|---|---|---|---|
| 4,552,707 A | 11/1985 | How | |
| 4,689,186 A | 8/1987 | Bornat | |
| 5,328,946 A | 7/1994 | Tuminello et al. | |
| 5,344,297 A | 9/1994 | Hills | |
| 5,509,902 A | 4/1996 | Raulerson | |
| 5,552,100 A | 9/1996 | Shannon et al. | |
| 5,562,986 A | 10/1996 | Yamamoto et al. | |
| 5,665,428 A | 9/1997 | Cha et al. | |
| 5,700,572 A | 12/1997 | Klatt et al. | |
| 5,702,658 A | 12/1997 | Pellegrin et al. | |
| 5,741,333 A | 4/1998 | Frid | |
| 5,941,910 A | 8/1999 | Schindler et al. | |
| 6,010,529 A | 1/2000 | Herweck et al. | |
| 6,436,135 B1 | 8/2002 | Goldfarb | |
| 6,498,207 B1 | 12/2002 | Hoshikawa et al. | |
| 6,517,571 B1 | 2/2003 | Brauker et al. | |
| 6,679,913 B2 | 1/2004 | Homsy | |
| 7,115,220 B2 | 10/2006 | Dubson et al. | |
| 7,244,272 B2 | 7/2007 | Dubson et al. | |
| 7,316,754 B2 | 1/2008 | Ide et al. | |
| 7,413,575 B2 | 8/2008 | Phaneuf et al. | |
| 7,416,559 B2 | 8/2008 | Shalaby | |
| 7,485,141 B2 | 2/2009 | Majercak et al. | |
| 7,524,527 B2 | 4/2009 | Stenzel | |
| 7,556,634 B2 | 7/2009 | Lee et al. | |
| 7,582,240 B2 | 9/2009 | Marin et al. | |
| 7,799,261 B2 | 9/2010 | Orr et al. | |
| 7,857,608 B2 | 12/2010 | Fabbricante et al. | |
| 7,947,069 B2 | 5/2011 | Sanders | |
| 7,981,353 B2 | 7/2011 | Mitchell et al. | |
| 8,178,030 B2 | 5/2012 | Anneaux et al. | |
| 8,257,640 B2 | 9/2012 | Anneaux et al. | |
| 8,262,979 B2 | 9/2012 | Anneaux et al. | |
| 8,691,543 B2 | 4/2014 | Gaudette et al. | |
| 8,771,582 B2 | 7/2014 | Phaneuf et al. | |
| 2001/0034549 A1* | 10/2001 | Bartholf et al. | 623/1.12 |
| 2002/0198588 A1 | 12/2002 | Armstrong | |
| 2003/0040772 A1 | 2/2003 | Hyodoh et al. | |
| 2003/0100944 A1 | 5/2003 | Laksin et al. | |
| 2003/0114917 A1 | 6/2003 | Holloway et al. | |
| 2003/0195611 A1* | 10/2003 | Greenhalgh et al. | 623/1.15 |
| 2003/0211135 A1 | 11/2003 | Greenhalgh et al. | |
| 2004/0016260 A1 | 1/2004 | Kobayashi et al. | |
| 2004/0030377 A1 | 2/2004 | Dubson et al. | |
| 2004/0033364 A1 | 2/2004 | Spiridigliozzi et al. | |
| 2004/0051201 A1 | 3/2004 | Greenhalgh et al. | |
| 2004/0054397 A1 | 3/2004 | Smith et al. | |
| 2004/0167606 A1 | 8/2004 | Chouinard | |
| 2005/0137675 A1 | 6/2005 | Dubson et al. | |
| 2005/0187605 A1 | 8/2005 | Greenhalgh et al. | |
| 2005/0244453 A1* | 11/2005 | Stucke et al. | 424/423 |
| 2006/0200232 A1 | 9/2006 | Phaneuf et al. | |
| 2007/0026036 A1* | 2/2007 | Falotico et al. | 424/423 |
| 2007/0031607 A1* | 2/2007 | Dubson et al. | 427/458 |
| 2007/0043428 A1 | 2/2007 | Jennings et al. | |
| 2007/0087027 A1 | 4/2007 | Greenhalgh et al. | |
| 2007/0207179 A1* | 9/2007 | Andersen et al. | 424/423 |
| 2007/0207186 A1 | 9/2007 | Scanlon et al. | |
| 2007/0244569 A1 | 10/2007 | Weber et al. | |
| 2007/0269481 A1 | 11/2007 | Li et al. | |
| 2007/0276477 A1 | 11/2007 | Lee et al. | |
| 2008/0021545 A1 | 1/2008 | Reneker et al. | |
| 2008/0029617 A1 | 2/2008 | Marshall et al. | |
| 2008/0118541 A1 | 5/2008 | Pacetti | |
| 2008/0119943 A1 | 5/2008 | Armstrong et al. | |
| 2008/0199506 A1 | 8/2008 | Horres et al. | |
| 2008/0208323 A1 | 8/2008 | El-Kurdi et al. | |
| 2008/0234812 A1 | 9/2008 | Pacetti | |
| 2008/0242171 A1 | 10/2008 | Huang et al. | |
| 2008/0281406 A1 | 11/2008 | Addonizio et al. | |
| 2008/0305143 A1 | 12/2008 | Chen et al. | |
| 2008/0319535 A1 | 12/2008 | Craven et al. | |
| 2009/0012607 A1 | 1/2009 | Kim et al. | |
| 2009/0018643 A1 | 1/2009 | Hashi et al. | |
| 2009/0082846 A1 | 3/2009 | Chobotov | |
| 2009/0088828 A1 | 4/2009 | Shalev et al. | |
| 2009/0136651 A1 | 5/2009 | Larsen et al. | |
| 2009/0160099 A1 | 6/2009 | Huang | |
| 2009/0163994 A1 | 6/2009 | Quigley et al. | |
| 2009/0227944 A1 | 9/2009 | Weber | |
| 2009/0248131 A1 | 10/2009 | Greenan | |
| 2009/0248144 A1 | 10/2009 | Bahler et al. | |
| 2009/0280325 A1 | 11/2009 | Lozano et al. | |
| 2010/0013126 A1 | 1/2010 | Ishaque et al. | |
| 2010/0093093 A1 | 4/2010 | Leong et al. | |
| 2010/0190254 A1 | 7/2010 | Chian et al. | |
| 2010/0233115 A1 | 9/2010 | Patel et al. | |
| 2010/0280590 A1 | 11/2010 | Sun et al. | |
| 2010/0304205 A1 | 12/2010 | Jo et al. | |
| 2010/0323052 A1 | 12/2010 | Orr et al. | |
| 2010/0331965 A1 | 12/2010 | Dugas et al. | |
| 2011/0030885 A1 | 2/2011 | Anneaux et al. | |
| 2011/0031656 A1 | 2/2011 | Anneaux et al. | |
| 2011/0089603 A1 | 4/2011 | Fabbricane et al. | |
| 2011/0135806 A1 | 6/2011 | Grewe et al. | |
| 2011/0142804 A1 | 6/2011 | Gaudette et al. | |
| 2011/0156319 A1 | 6/2011 | Kurokawa et al. | |
| 2011/0263456 A1 | 10/2011 | Hartig | |
| 2011/0295200 A1 | 12/2011 | Speck et al. | |
| 2012/0114722 A1 | 5/2012 | Ballard et al. | |
| 2012/0292810 A1 | 11/2012 | Peno et al. | |
| 2012/0316633 A1* | 12/2012 | Flanagan et al. | 623/1.11 |
| 2013/0023175 A1 | 1/2013 | Anneaux et al. | |
| 2013/0053948 A1 | 2/2013 | Anneaux et al. | |
| 2013/0059497 A1 | 3/2013 | Anneaux et al. | |
| 2013/0079700 A1 | 3/2013 | Ballard et al. | |
| 2013/0238086 A1 | 9/2013 | Ballard et al. | |
| 2013/0268062 A1 | 10/2013 | Puckett et al. | |
| 2013/0316103 A1 | 11/2013 | Anneaux et al. | |

FOREIGN PATENT DOCUMENTS

| | | | |
|---|---|---|---|
| WO | WO 2005018600 A2 * | 3/2005 | |
| WO | 2006123340 | 11/2006 | |
| WO | WO2007075256 | 7/2007 | |
| WO | WO2009/127170 | 10/2009 | |
| WO | WO2009146280 | 12/2009 | |
| WO | WO2010132636 | 11/2010 | |
| WO | WO2012103501 | 8/2012 | |

OTHER PUBLICATIONS

Restriction Requirement dated Sep. 26, 2013 for U.S. Appl. No. 13/742,025.
International Search Report and Written Opinion dated Sep. 6, 2013 for PCT/US2013/046245.
U.S. Appl. No. 13/360,444, filed Jan. 27, 2012, Eller et al.
U.S. Appl. No. 13/826,618, filed Mar. 14, 2013, Hall et al.
International Search Report and Written Opinion dated May 23, 2012 for PCT/US2012/023006.
U.S. Appl. No. 13/827,775, filed Mar. 14, 2013, Lampropoulos et al.
U.S. Appl. No. 13/829,452, filed Mar. 14, 2013, Hall et al.
International Search Report and Written Opinion dated Sep. 17, 2013 for PCT/US2013/060172.
International Search Report and Written Opinion dated Dec. 5, 2013 for PCT/US2013/060812.
U.S. Appl. No. 14/207,344, filed Mar. 12, 2014, Mower et al.
Office Action dated Mar. 3, 2014 for U.S. Appl. No. 13/742,025.
Office Action dated May 9, 2014 for U.S. Appl. No. 13/360,444.
Office Action dated Jul. 2, 2014 for U.S. Appl. No. 14/044,050.
International Search Report and Written Opinion dated Apr. 26, 2013 for PCT/US2013/021554.
U.S. Appl. No. 13/742,077, filed Jan. 15, 2013, Hall et al.
U.S. Appl. No. 13/742,025, filed Jan. 15, 2013, Hall et al.
Office Action dated Oct. 10, 2014 for U.S. Appl. No. 13/742,025.
European Search Report dated Aug. 19, 2014 for EP12755426.9.
Office Action dated Jan. 13, 2015 for U.S. Appl. No. 13/827,790.
Office Action dated Feb. 4, 2015 for U.S. Appl. No. 13/360,444.
Office Action dated Feb. 20, 2015 for U.S. Appl. No. 14/044,050.
Office Action dated Feb. 26, 2015 for U.S. Appl. No. 14/152,590.

(56) References Cited

OTHER PUBLICATIONS

International Search Report and Written Opinion dated Jun. 26, 2014 for PCT/US2014/024868.
International Search Report and Written Opinion dated Jul. 1, 2014 for PCT/US2014/023416.
International Report on Patentability dated Jul. 22, 2014 for PCT/US2013/021554.
Office Action dated Aug. 29, 2014 for U.S. Appl. No. 14/152,590.
U.S. Appl. No. 14/204,466, filed Mar. 11, 2014, Hall et al.
Office Action dated Jul. 29, 2015 for U.S. Appl. No. 14/152,626.
Office Action dated Aug. 10, 2015 for U.S. Appl. No. 14/044,050.
Extended European Search Report dated Jun. 25, 2015 for EP12739348.6.
International Preliminary Report dated Jul. 30, 2013 for PCT/US2012/023006.

* cited by examiner

DRUG-ELUTING ROTATIONAL SPUN COATINGS AND METHODS OF USE

RELATED APPLICATIONS

This application claims priority to U.S. Provisional Application No. 61/704,212 filed on Sep. 21, 2012, titled Drug-Eluting Rotational Spun Coatings and Method of Use, which is hereby incorporated by reference in its entirety herein.

TECHNICAL FIELD

The present disclosure relates generally to rotational spun coatings that include a therapeutic agent and may be used to coat a medical device. The disclosure also relates to medical devices, such as balloon catheters, stents, catheters and vascular grafts, which are coated with drug-eluting rotational spun materials that may be used to deliver a therapeutic agent to a particular tissue or body lumen.

BRIEF DESCRIPTION OF THE DRAWINGS

The embodiments disclosed herein will become more fully apparent from the following description and appended claims, together with the accompanying drawings. These drawings depict only typical embodiments, which will be described with additional specificity and detail through use of the accompanying drawings, in which:

DETAILED DESCRIPTION

Figure 1A:
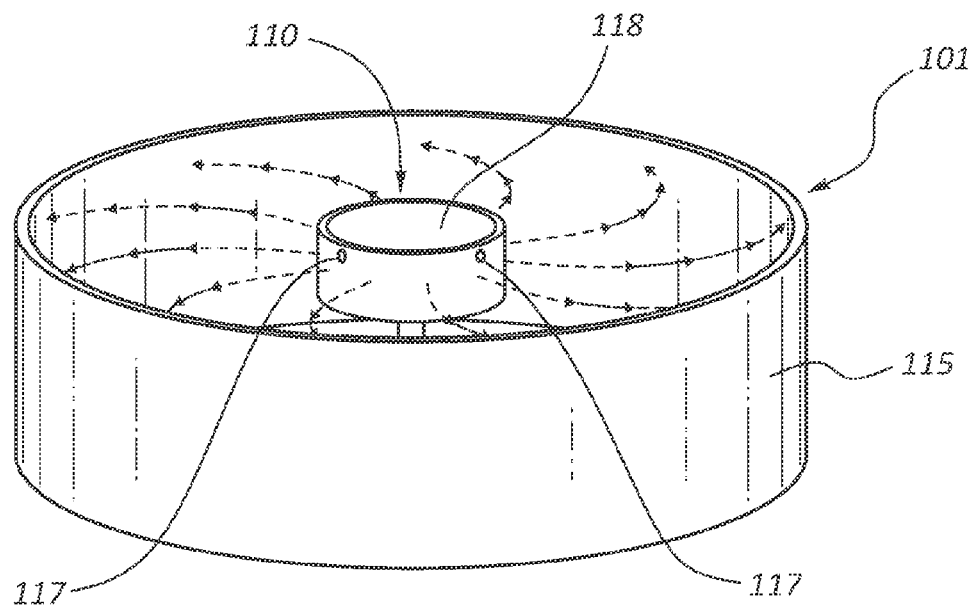
FIG. 1A is a perspective view of a rotational spinning apparatus.

A variety of medical treatments or diagnostics may be performed by inserting and/or implanting medical devices into the circulatory system or other body lumens of a subject. For example, medical devices that may be used for the treatment of vascular disease include stents, catheters, balloon catheters, guide wires and cannulas. The use of inserted and/or implanted medical devices may cause undesired complications such as injury to the endothelium and to smooth muscle cells in the vasculature, which can result in thrombus deposition, inflammation, leukocyte and macrophage infiltration, smooth muscle cell proliferation/migration, restenosis, fibrosis and extracellular matrix deposition. Moreover, the use of insertable and/or implantable medical devices can lead to neointimal growth and lumen compromise.

A coating on a medical device may be configured to inhibit or reduce inflammatory responses by the body in response to the device. For example, a medical device configured to permit tissue ingrowth and/or the growth or attachment of endothelial cells onto blood contacting surfaces of the device may reduce the likelihood of negative flow characteristics and thrombosis formation. Similarly, a device so configured may mitigate the body's inflammatory response toward the material on, for example, the tissue or non-blood contacting surfaces of the device. Such a coating may include a drug-eluting coating comprising a chemical or therapeutic agent for disease treatment and/or to reduce or inhibit inflammation or tissue injury that may result from the presence of the device. By limiting or inhibiting the potential inflammatory response or reaction to a medical device, negative outcomes such as the presence of inflammatory macrophages and foreign-body giant cells may be reduced. This may aid in minimizing, for example, the chain of biological responses that result in fibrous capsule formation surrounding the device and neointimal hyperplasia.

Disclosed herein are rotational spun coatings and medical devices that may be used to reduce or inhibit the complications that can accompany the use of medical devices in the circulatory system or within other body lumens of a subject. The medical devices disclosed herein are coated with drug-eluting rotational spun material containing a therapeutic agent for delivery to a target tissue. Also disclosed herein are methods for preparing drug-eluting rotational spun material and methods of coating medical devices with such material, as well as methods of drug delivery using medical devices that are coated with drug-eluting rotational spun material comprising at least one therapeutic agent.

The terms, "drug", "therapeutic agent", "active agent", "chemical", "additive" and other related terms may be used interchangeably herein. A therapeutic agent may be used singly or in combination with other therapeutic agents.

The terms "drug-eluting" and "drug-releasing" and other related terms may be used interchangeably herein. These terms are meant to describe the association of a therapeutic agent with a coating, and refer to the connection between the therapeutic agent and the coating. This association includes, for example, covalent, non-covalent, ionic, electrostatic, dipole-dipole, Van der Waals's, hydrogen bonding, hydrophilic, and hydrophobic bonding interactions. In certain embodiments, the therapeutic agent is associated with a drug-eluting rotational spun coating via covalent or ionic bonding.

The medical devices as disclosed herein comprise rotational spun materials that at least partially coat or cover the medical device. The terms "coating", "covering", and other related terms may be used interchangeably herein, as may the terms "medical device", "appliance", "substrate", "mat" or "structure." The present disclosure is applicable to any implantable medical device, notwithstanding any specific examples included herein. In other words, although particular medical devices such as balloons, stents, catheters, grafts or patches may be referenced in the disclosure and examples herein, the disclosure is also analogously applicable to other medical devices or appliances that may comprise a coating or layer of polymeric material.

In some embodiments, rotational spun materials such as rotational spun nanofibers (i.e. fibers which are smaller than one micron in diameter) or microfibers (i.e. fibers which are between one micron and one millimeter in diameter), may be configured to permit interaction with nanoscale structures within a body, such as endothelial cells. Rotational spinning refers generally to processes involving the expulsion of flowable material from one or more orifices, the material forming fibers which are subsequently deposited on a collector. Examples of flowable materials include, for example, dispersions, solutions, suspensions, liquids, molten or semi-molten material, and other fluid or semi-fluid materials. In particular embodiments, the rotational spun materials disclosed herein may include at least one of nylon 6-6, polyethylene, polypropylene, PTFE, Kevlar, and other polymers or mixtures thereof. Other suitable polymeric materials include polyolefins, such as ethylene and propylene homopolymers, as well as any copolymers of ethylene and propylene such as ethylene-vinyl acetate copolymers, ethylene (meth)acrylate copolymers, ethylene n-butyl acrylate copolymers, and grafted polyolefins such as maleic anhydride grafted polyethylene or polypropylene. Other suitable polymers which may be employed in the rotational spun coatings include, but are not limited to, polyesters, polyamides including nylon 12, polyurethanes, polyethers, polyimides, polycarboxylic acids including polyacrylic acids, (meth)acrylates, cellulosics, polycaprolactams, polyacrylamides, polycarbonates, polyacrylonitriles, polyvinylpyrrolidones, and copolymers thereof.

In some embodiments, the drug-eluting rotational spun coating comprises at least one of nylon 6-6, polyethylene, polypropylene, PTFE, and Kevlar.

In certain embodiments, the rotational spun materials disclosed herein can include biomolecules such as fibrin, fibrinogen, chitin, chitosan, starch, collagen, hyaluronic acid, alginate and other natural polymers, polysaccharides such as dextran and cellulose, and mixtures thereof. In some embodiments, the drug-eluting rotational spun coating comprises at least one of fibrin, fibrinogen, chitin, chitosan, starch, collagen, hyaluronic acid, alginate, dextran, cellulose, and mixtures thereof. In further embodiments, the rotational spun materials as disclosed herein may include bioresorbable polymers. Examples of bioresorbable polymers include, but are not limited to, polyhydroxyalkanoates such as poly(hydroxybutyrate) (PHB), poly(hydroxyvalerate) (PHV) and poly(hydroxybutyrate-co-valerate) (PHBV), polylactones such as polycaprolactone (PCL), poly(L-lactic acid) (PLA), poly(glycolic acid) (PGA), poly(lactide-co-glycolide) (PLGA), polydioxanone, polyorthoesters, polyanhydrides, poly(D,L-lactic acid), poly(lactide-co-caprolactone), poly(glycolic acid-co-trimethylene carbonate), polyphosphoesters, polyphosphoester urethanes, poly(amino acids), polyacrylates, cyanoacrylates, poly(trimethylene carbonate), polyurethanes, poly(iminocarbonate), copoly(ether-esters) (e.g. PEO/PLA), polyalkylene oxalates, and polyphosphazenes.

In certain embodiments, a rotational spinning process comprises loading a polymeric solution or dispersion into a cup or spinneret configured with orifices on the outside circumference of the spinneret. The spinneret is then rotated, causing (through a combination of centrifugal and hydrostatic forces, for example) the flowable material to be expelled from the orifices. The material may then form a "jet" or "stream" extending from the orifice, with drag forces tending to cause the stream of material to elongate into a small diameter fiber. The fibers may then be directly deposited on a medical device or on a collection apparatus. In some embodiments, the rotational spinning processes are completed in the absence of an electric field. Exemplary methods and systems for rotational spinning can be found in U.S. Patent Publication No. US2009/0280325, titled "Methods and Apparatuses for Making Superfine Fibers," which is incorporated herein by reference in its entirety.

In other embodiments, electrospun materials may be used as a medical device coating. "Electrospinning" refers to a process for forming mats, tubes, or other shapes by depositing small strings of material fibers on charged surfaces. The electrospinning process controls the thickness, density, porosity, and other characteristics of the spun material so formed. Electrospinning is described in U.S. Pat. No. 8,178,030 titled "Electrospinning of PTFE with High Viscosity Materials," and in U.S. patent application Ser. No. 13/360,444, titled "Electrospun PTFE Coated Stent and Method of Use," which are both herein incorporated by reference in their entirety. In certain embodiments, the medical device may comprise an electrospun coating in addition to the rotational spun coating.

Rotational spinning may be configured to create mats, tubes, or other structures comprised of elongate fibers, including nanofibers (i.e. fibers which are smaller than about one micron in diameter) or microfibers (i.e. fibers which are between about one micron and about one millimeter in diameter). In some instances the fibers may be randomly disposed, while in other embodiments the alignment or orientation of the fibers may be somewhat controlled or follow a general trend or pattern. Regardless of any pattern or degree of fiber alignment, as the fibers are deposited on a medical device or collector or on previously deposited fibers, the fibers are not woven but rather serially deposited on the device, collector or other fibers. Because rotational spinning may be configured to create a variety of structures, as used herein, the terms "mat" or "non-woven mat or material" are intended to be broadly construed as referring to any such rotational spun or electrospun structure, including coatings, coverings, tubes, and spheres.

The present disclosure relates to medical devices which may have, in certain embodiments, a structure or element covered with at least one layer of a drug-eluting rotational spun coating. In some embodiments, the medical devices disclosed herein may have a polymeric or metal structure or element covered with at least one layer of rotational spun material. For example, the drug-eluting rotational spun coating may comprise at least two layers of rotational spun fibers. In certain embodiments, the drug-eluting rotational spun coating may comprise at least one layer of rotational spun fibers and at least one layer of a non-spun material. In other embodiments, the present disclosure relates to medical devices or appliances formed of rotational spun materials which may have structures and/or elements which are made of any appropriate material and are formed in any desired shape. It will be appreciated that, although particular structures and coverings are described herein, any feature of the covering or scaffolding described herein may be combined with any other disclosed feature without departing from the scope of the current disclosure.

The medical devices disclosed herein have a drug-eluting rotational spun coating comprising a therapeutic agent for delivery to a site in the body. In particular embodiments, the drug-eluting rotational spun coating on a medical device disclosed herein may be used to deliver a drug and/or to reduce or inhibit inflammation or tissue injury that may be caused by the device. In other embodiments, the drug-eluting rotational spun coating may be used for the targeted delivery of a therapeutic agent to any location or tissue. In certain embodiments, the rotational spun coating on a medical device disclosed herein may be used for the targeted delivery of a therapeutic agent to a tissue during or following a medical procedure, for example, to treat or prevent vascular and nonvascular diseases such as restenosis.

In an embodiment, a medical device comprises a drug-eluting rotational spun coating, wherein the drug-eluting rotational spun coating comprises a therapeutic agent in an amount configured to deliver a pharmaceutically effective dose to a target tissue.

In some embodiments, the drug-eluting rotational spun coatings disclosed herein comprise a therapeutic agent that has been incorporated into the rotational spun coating according to methods known by those of skill in the art with the aid of the present disclosure. In certain embodiments, the therapeutic agent can be mixed with a solution of flowable material before it is rotationally spun onto a medical device. In such embodiments, the therapeutic agent may be mixed with a solution of flowable material comprising, for example, one or more dispersions, carrier solutions, suspensions, liquids, molten or semi-molten materials, or other fluid or semi-fluid material. In one such embodiment, the therapeutic agent is mixed with a carrier solution and is then rotationally spun onto a medical device, thereby providing a therapeutic agent associated with the rotational spun fibers.

In other embodiments, the drug-eluting rotational spun coatings disclosed herein comprise a therapeutic agent that has been applied to the rotational spun coating after the coating has been applied to the medical device or collector. The therapeutic agent can be, for example, sprayed or painted onto the rotational spun coating. In some embodiments, the rotational spun coating can be dipped or rolled in the therapeutic agent. In certain embodiments, the therapeutic agent is associated with the drug-eluting rotational spun coating during the rotational spinning of the drug-eluting rotational spun coating. In other embodiments, the therapeutic agent is associated with the drug-eluting rotational spun coating subsequent to the rotational spinning of the drug-eluting rotational spun coating.

In certain embodiments, the therapeutic agent may be selected from at least one of paclitaxel, rapamycin, beta-lapachone, vitamin D, a bismuth-containing compound, heparin, iopromide or other contrast agent, analogs of any of the foregoing, and mixtures thereof. In some embodiments, the therapeutic agent is selected from at least one of rapamycin, paclitaxel, a bismuth-containing compound, heparin, and analogs of any of the foregoing. In other embodiments, the therapeutic agent may be present in combination with a second therapeutic agent. For example, the therapeutic agent is at least one of paclitaxel, rapamycin, heparin, and analogs thereof, and the second therapeutic agent is at least one of beta-lapachone, vitamin D, and their analogs. In further embodiments, the therapeutic agent may be selected from at least one of rapamycin (also known as sirolimus), fujimycin (also known as tacrolimus), umirolimus, an antibiotic, an antifungal agent, an autophagy activator, an enzyme, an enzyme inhibitor, a protein including an antibody, an immunoregulator, a kinase, and a phosphatase. In still further embodiments, the therapeutic agent may include one or more steroids, immunosuppressants, anti-proliferatives, proliferatives, anti-infectives, anti-thrombotics, thrombotics, nutritional additives, prophylactics, or preventative agents. In an embodiment, the therapeutic agent is dexamethasone. In further embodiments, the therapeutic agent may be a cell or mixture of cells, for example, for use in skin grafts, tissue engineering, bone regrowth or similar prosthetic indications. The therapeutic agent may be present in a salt form or as a prodrug.

In some embodiments, the drug-eluting rotational spun coating on a medical device disclosed herein can increase the polymeric surface area of the medical device, which may improve the delivery of the associated therapeutic agent to a target tissue. Without being bound by theory, the additional surface area provided by the rotational spun coating may increase the contact area between the drug-eluting rotational spun coating on the medical device and a target tissue and/or biological fluid. For certain embodiments described herein, the release rate of the therapeutic agent may be generally proportional to the surface area of the drug-eluting rotational spun coating on the medical device. In other embodiments, the increased surface area created by the rotational spun coating may increase the rate of delivery of the therapeutic agent.

In certain embodiments, the drug-eluting rotational spun coating of a medical device may allow for a controlled release, such as an immediate release, of an effective dose of a therapeutic agent to a target tissue. In particular embodiments, the drug-eluting rotational spun coating on the surface of a medical device may allow for the relatively rapid release of an effective dose of a therapeutic agent to a target tissue in approximately 5 minutes or less. In some embodiments, the drug-eluting rotational spun coating on the surface of a medical device may allow for the controlled release of an effective dose of a therapeutic agent to a target tissue in approximately 5 minutes or less, 4 minutes or less, 3 minutes or less, 2.5 minutes or less, 2 minutes or less, 1.8 minutes or less, 1.6 minutes or less, 1.4 minutes or less, 1.2 minutes or less, 1 minute or less, 0.9 minutes or less, 0.8 minutes or less, 0.7 minutes or less, 0.6 minutes or less, 0.5 minutes or less, 0.4 minutes or less, 0.3 minutes or less, 0.2 minutes or less, or 0.1 minutes or less.

In other embodiments of a medical device as disclosed herein, the increased surface area created by the rotational spun coating may increase the bioavailability of a therapeutic agent. Without being bound by theory, the increased surface area created by the rotational spun coating may provide for a more efficient release of the therapeutic agent and an increased drug absorption by the target tissue. In such embodiments, the increased surface area created by the rotational spun coating can allow for a reduction in the amount of therapeutic agent that is used to deliver an effective dose, in comparison to the amount used without a rotational spun coating. In certain such embodiments, the increased surface area created by the rotational spun coating may allow an effective dose of therapeutic agent to be delivered to the target tissue while using approximately less than 10%, 20%, 30%, 40%, 50%, 60%, 70%, 80%, or 90% of the therapeutic agent used without the presence of a drug-eluting rotational spun coating on the medical device.

In certain embodiments of the medical devices disclosed herein, the surface area of the rotational spun coating may be adjusted by increasing or decreasing the density or fiber size of the rotational spun material on the medical device. In other embodiments, the medical device may be coated with one or more layers of a rotational spun material wherein the various layers may be in different orientations relative to each other. In some embodiments, the surface area of the rotational spun coating may be adjusted in order to control the delivery rate of the associated therapeutic agent. In some embodiments, the rotational spun layers can be coupled with non-spun layers, including, for example, expanded PTFE or sheets, films and tubes of other polymeric or biological materials.

In further embodiments of the medical devices disclosed herein, the drug-eluting rotational spun coating may be configured to provide a controlled release, such as a delayed release, of the associated therapeutic agent. In certain such embodiments, the medical device may be coated with one or more layers of a drug-eluting rotational spun material wherein the one or more layers of the drug-eluting rotational spun material are configured to control the release of the therapeutic agent over a desired period of time while the medical device is in place. For example, the one or more layers of rotational spun materials may comprise alternating layers of drug-eluting rotational spun material with non-drug-eluting rotational spun material or other manufactured material. In other embodiments, the medical device may be coated with one or more layers of a drug-eluting rotational spun material wherein the one or more layers of the drug-eluting rotational spun material are covered with one or more additional controlled release layers that are configured to delay or otherwise control the release of the therapeutic agent into the target tissue.

In an embodiment, the release of the therapeutic agent may be controlled by varying its tortuous path through the rotational spun material. In an analogous manner to the flow of analyte in chromatographic separations, the rotational spun material comprising a drug-eluting coating can be considered to be the solid phase and the therapeutic agent can be considered to be the analyte. In size exclusion or gel permeation chromatography, the analyte has no interaction, chemically or physically, with the solid phase and the flow of analyte occurs solely on the basis of its hydrodynamic volume. In these situations, a larger analyte, such as a larger therapeutic agent, takes a shorter, less tortuous path through a porous solid phase, such as the drug-eluting rotational spun material, and so it is released more quickly from the material. Smaller therapeutic agents may pass into the pores or interstices and therefore take a longer, more tortuous path through the material, becoming released more slowly from the material.

Alternatively, in some situations, the release of a larger therapeutic agent can be inhibited by the drug-eluting rotational spun material. In ion exchange chromatography, analytes are retained on the solid phase based on their ionic characteristics. An analyte would be retained on the solid phase if it is ionically attracted by the solid phase, and would be excluded if it is repelled by the solid phase. In certain embodiments wherein the analyte and solid phase are ionically attracted, a larger therapeutic agent would take a longer period of time to pass through, and be released from, the rotational spun material due to the longer tortuous path length. The porosity of the rotational spun material may vary to affect the tortuous path length, as well. For example, a rotational spun material with micro sized pores or with a high porosity may release a therapeutic agent more quickly than a material with nano sized pores or a low porosity.

In some embodiments, the drug-eluting rotational spun coating is configured to provide a controlled release of a therapeutic agent to a target tissue over a time period of at least approximately one day, multiple days, a week, multiple weeks, a month, multiple months, a year, or a year or greater.

In further embodiments, the medical device may be coated with one or more layers of a biodegradable and/or bioabsorbable drug-eluting rotational spun material that may be configured to control the release of a therapeutic agent into a target tissue. In certain embodiments, the medical device may be coated with one or more layers of a drug-eluting rotational spun material comprising one or more bioabsorbable polymers (e.g., polyhydroxyalkanoates, poly-3-hydroxybutyrate, polyamide 11, PLA and PLGA, and/or one or more bioabsorbable metallics (e.g., zinc, magnesium, and cadmium). In specific embodiments, the medical device may be coated with one or more layers of a drug-eluting rotational spun material configured to control the release of the therapeutic agent, selected from at least one of chitin, chitosan, collagen, fibrin, and cellulose.

Drug-eluting rotational spun material may similarly be used to alter the surface characteristics of various medical devices. In an embodiment, a medical device such as a catheter may be coated with one or more layers of a drug-eluting rotational spun material configured to change the hydrophobicity of the catheter surface.

In certain embodiments, the rotational spun material may be used to form a scaffold for use in tissue engineering or bone/skin graft applications. For example, a scaffold may be configured to permit tissue ingrowth and/or cell attachment by the appropriate selection of polymer and pore size/density. In an embodiment, a scaffold may be configured for use in skin grafts or for bone regrowth, such as for prosthetic vertebrae. In some embodiments, the rotational spun material may be configured to improve the surface interactions of medical implants, such as hip implants.

In some embodiments, the rotational spun material may be used to form polymeric particles for delivering drugs. The polymeric particles may be formed by, for example, grinding, milling or crushing the rotationally spun material into any shape. In an embodiment, microspheres which are substantially spherical in shape may be formed. The microspheres may have diameters ranging from between about 10 µm to about 2000 µm. The polymeric particles may be implanted, for example, and may be injectable through a needle of 18 gauge or smaller. In certain embodiments, the polymeric particles may be biodegradable and/or bioabsorbable. In other embodiments, the polymeric particles are not biodegradable. A variety of therapeutic agents may be associated with the polymeric particles, including for example, anti-thrombotic drugs, proteins and bismuth-containing compounds. The polymeric particles may comprise multiple layers of rotational spun material, or may comprise layers of material which are not rotationally spun in combination with the rotational spun material. In certain embodiments, the polymeric particles may comprise a rotational spun coating which associates the therapeutic agent via ionic, hydrophobic or hydrophilic interactions. The polymeric particles may contain a surfactant and/or a charged or functionalizable group, such as an acid or an amine. In some embodiments, the association of the therapeutic agent is via a covalent bond.

In certain related embodiments, the polymeric particles may be used to deliver a drug via the respiratory tract as, for example, an aerosol. The polymeric particles may act as carrier particles to aid in dispersing the therapeutic agent within the aerosol. Exemplary therapeutic agents include bronchodilating agents, anticholinergics, steroids, proteins including antibodies, and combinations thereof. The polymeric particles may have an optical diameter of about 7 µm or less, for example, between 1 µm and 500 nm. The polymeric particles may contain a surfactant and/or a charged or functionalizable group, such as an acid or an amine.

The rotational spun material may be used, for example, for a transdermal membrane or a device configured for transdermal drug delivery. In such embodiments, the drug-eluting rotational spun material may release the therapeutic agent in a controlled manner, such as over a time period of at least approximately one day, multiple days, a week, multiple weeks, a month, multiple months, a year, or a year or greater. The device may comprise multiple layers of rotational spun material, or may comprise layers of material which are not rotationally spun in combination with the rotational spun material.

In some embodiments of the medical devices comprising a drug-eluting rotational spun coating disclosed herein, the rotational spun coating may be configured to provide a controlled release, such as an immediate release or a delayed release, of the associated therapeutic agent. In certain embodiments, the drug-eluting rotational spun material may be configured to release a dose of a therapeutic agent to a target tissue of between about 100 µg and about 600 µg over a desired period of time. In certain such embodiments, the drug-eluting rotational spun material may be configured to release a dose of a therapeutic agent of at least about 100 µg, 150 µg, 200 µg, 250 µg, 300 µg, 350 µg, 400 µg, 450 µg, 500 µg, 550 µg, and 600 µg over a desired period of time.

The medical devices disclosed herein include balloons and balloon catheters that comprise a drug-eluting rotational spun coating. In some embodiments, a balloon may be introduced into a patient's body in a low-profile, deflated configuration, inflated to perform a stage of a therapy, and then deflated for removal. Balloons, balloon catheters, or other inflatable medical devices may be used in connection with, for example, angioplasty, valvuloplasty, stent placement or expansion, stenotic vessels, and stenotic heart valves. In certain embodiments, balloons may comprise a multilayered design, including embodiments wherein one or more layers comprise a drug-eluting rotational spun coating. In further embodiments, the medical devices disclosed herein may comprise balloons or balloon catheters having multilayered designs configured to strengthen or otherwise affect certain properties of the balloon, including mechanical properties such as burst strength and puncture resistance.

The term "balloon" is used broadly throughout this disclosure to refer to a variety of inflatable medical devices and appliances having a variety of shapes, characteristics, and uses. Further, disclosure or concepts provided in connection with embodiments or examples reciting particular shapes, structures, or uses may be analogously applied to any inflatable medical device.

A balloon including a drug-eluting rotational spun material as described herein, may comprise a wall defining the interior portion of the balloon and separating the interior portion from the external environment. As the balloon is inflated, fluid may be introduced into the interior portion, exerting pressure on the wall of the balloon. In some therapies, the wall may be used to exert pressure on structures or objects outside the balloon. For example, a balloon may be inflated within a body lumen at the location of a blockage or other stricture, the wall of the balloon being used to break up the blockage or force it toward the lumen wall. Similarly, a balloon may be used to exert an expansive force on a stent, to deploy the stent and force it to come in contact with a body lumen wall. In some embodiments, balloons may be configured with a "flow through" type design, which may allow blood or other fluids to pass through the balloon while the balloon is inflated. For example, a balloon may be shaped like a hollow cylinder, allowing the balloon to be inflated within a blood vessel to exert pressure on the vessel wall, while still allowing blood to pass through the center of the balloon.

In certain embodiments of medical devices with a "flow through" type design, such as an embolic filter balloon, a drug-eluting coating may be configured such that the therapeutic agent is released in a controlled manner as blood or other fluids pass through the balloon. In some embodiments, the therapeutic agent may be an anti-thrombotic agent used to reduce thrombosis formation on the filter.

The medical devices disclosed herein may comprise balloons formed of a variety of materials, including elastomers, polymers, Kevlar, flexible materials, and rotational spun materials. Specifically, in some embodiments, balloons may be formed of PEBAX, nylon, silicone, or thermoplastic material.

In some embodiments, a balloon may include a coating comprising multiple layers including at least one drug-eluting rotational spun layer. In certain embodiments, coating a balloon with one or more rotational spun layers may increase the burst strength, puncture resistance, or other property of the balloon. In further embodiments, the type of coating materials used, the position, orientation and thickness of the layers, the size of the balloon, and other factors may be adjusted to create the desired elasticity and/or strength of the coated balloon. In other embodiments, the balloons as disclosed herein may comprise a rotational spun coating including one or more layers of the same material, or one or more layers of different materials. In some instances, a balloon coating may comprise one, two, three, four, or five layers of material, including at least one layer of a drug-eluting rotational spun material. In still other embodiments, a balloon coating may be formed of up to 10 layers of material or more, including at least one layer of a drug-eluting rotational spun material.

In certain embodiments, a balloon as disclosed herein may comprise one or more layers of a drug-eluting rotational spun coating designed to contact a target tissue upon inflation of the balloon. In such embodiments, the drug-eluting rotational spun coating is configured to contact the target tissue upon inflation of the balloon and then can be removed from the target tissue upon deflation or retraction of the balloon. In other embodiments, a balloon may comprise one or more layers of a drug-eluting rotational spun coating designed to contact a target tissue upon inflation of the balloon, and then the rotational spun coating can be separated from the balloon and left in place at the target tissue after deflation or retraction of the balloon.

In some embodiments, a balloon or balloon catheter as disclosed herein may comprise a drug-eluting rotational spun coating that effectively increases the surface area of the balloon, thereby improving the delivery of a therapeutic agent to a target tissue. In other embodiments, the increased surface area created by the rotational spun coating may increase the rate of delivery of the therapeutic agent by the balloon. In certain embodiments, the drug-eluting rotational spun coating on the surface of a balloon may allow for an immediate release of an effective dose of a therapeutic agent to a target tissue. In particular embodiments, the drug-eluting rotational spun coating on the surface of a balloon may allow for a relatively rapid release of an effective dose of a therapeutic agent to a target tissue in approximately 5 minutes or less. In some embodiments, the drug-eluting rotational spun coating on the surface of a balloon may allow for a relatively rapid release of an effective dose of a therapeutic agent to a target tissue in approximately 5 minutes or less, 4 minutes or less, 3 minutes or less, 2.5 minutes or less, 2 minutes or less, 1.8 minutes or less, 1.6 minutes or less, 1.4 minutes or less, 1.2 minutes or less, 1 minute or less, 0.9 minutes or less, 0.8 minutes or less, 0.7 minutes or less, 0.6 minutes or less, 0.5 minutes or less, 0.4 minutes or less, 0.3 minutes or less, 0.2 minutes or less, or 0.1 minutes or less.

In other embodiments of a balloon or balloon catheter disclosed herein, the increased surface area created by the rotational spun coating may increase the bioavailability of the therapeutic agent. The term "bioavailability" as used herein refers broadly to the exposure of the therapeutic agent to the subject. In some embodiments, the increased surface area of the rotational spun coating may provide for a more efficient release or elution of the therapeutic agent to the tissue, thereby allowing a reduction in the amount of therapeutic agent that is used to deliver an effective dose.

In certain embodiments of the balloons and balloon catheters disclosed herein, the surface area of the rotational spun coating may be adjusted by increasing or decreasing the density or fiber size of the rotational spun material on the balloon. In other embodiments, the balloon may be coated with one or more layers of a rotational spun material wherein the various layers may be in different orientations relative to each other. In some embodiments, the surface area of the rotational spun coating on the balloon may be adjusted in order to control the delivery of a therapeutic agent.

In further embodiments of the balloons or balloon catheters disclosed herein, the drug-eluting rotational spun coating may be configured to provide a controlled release of a therapeutic agent. In certain such embodiments, the balloon may be coated with one or more layers of a drug-eluting rotational spun material, wherein the one or more layers of the drug-eluting rotational spun material are configured to control, such as delay, the release of the therapeutic agent over a desired period of time while the balloon is in place. For example, the one or more layers of rotational spun materials may comprise alternating layers of drug-eluting rotational spun material with non-drug-eluting rotational spun material. In other such embodiments, the balloon may be coated with one or more layers of a drug-eluting rotational spun material wherein the one or more layers of the drug-eluting rotational spun material are covered with one or more additional controlled release layers that are configured to control the release of the therapeutic agent from the balloon. In further embodiments, the balloon may be coated with one or more layers of a biodegradable and/or bioabsorbable drug-eluting rotational spun material that may be configured to control the release of the therapeutic agent into the target tissue. In such embodiments, the material may be selected from at least one of bioabsorbable polymers (e.g., polyhydroxyalkanoates, poly-3-hydroxybutyrate, polyamide 11, PLA, and PLGA), bioabsorbable metallics (e.g., zinc, magnesium, and cadmium), chitin, chitosan, collagen, fibrin, and cellulose.

In some embodiments of the balloons or balloon catheters disclosed herein comprising a drug-eluting rotational spun coating, the rotational spun material may be configured to provide an immediate release or a delayed release of a therapeutic agent. In such embodiments of a balloon coating, the drug-eluting rotational spun material may be configured to release a dose of a therapeutic agent of approximately between 100 μg and 600 μg over a desired period of time.

In certain embodiments, the balloons or balloon catheters as disclosed herein comprise a drug-eluting rotational spun coating comprising a therapeutic agent with a concentration density from about 1 to about 20 μg/mm$^2$, or from about 2 to about 6 μg/mm$^2$. In certain embodiments, the balloon comprising a drug-eluting rotational spun coating comprises a therapeutic agent selected from at least one of paclitaxel and analogs thereof or rapamycin and analogs thereof.

Also disclosed herein are medical devices including stents with drug-eluting rotational spun coatings. Stents may be deployed, for example, in the central venous system for a variety of therapeutic purposes including the treatment of occlusions within the lumens of that system. The current disclosure may be applicable to stents or other medical devices and appliances designed for the central venous ("CV") system, peripheral vascular ("PV") stents, abdominal aortic aneurism ("AAA") stents, bronchial stents, esophageal stents, biliary stents, coronary stents, gastrointestinal stents, neuro stents, thoracic aortic endographs, or any other stent or stent graft.

As used herein, the term stent refers to a medical device configured for use within a bodily structure, such as within a body lumen. A stent may comprise a scaffolding or support structure and/or a covering. Thus, as used herein, "stent" refers to both covered and uncovered scaffolding structures.

In some embodiments, a stent as disclosed herein may comprise a drug-eluting rotational spun coating that effectively increases the surface area of the stent covering. In an embodiment, the increased surface area may improve the elution or delivery of a therapeutic agent to a target tissue. In other embodiments, the increased surface area created by the rotational spun coating may increase the rate of delivery of the therapeutic agent by the stent. In certain embodiments, the drug-eluting rotational spun coating on the surface of a stent may allow for an immediate release of an effective dose of a therapeutic agent to a target tissue. In particular embodiments, the drug-eluting rotational spun coating on the surface of a stent may allow for a relatively rapid release of a pharmaceutically effective dose of a therapeutic agent to a target tissue in approximately 5 minutes or less. In some embodiments, the drug-eluting rotational spun coating on the surface of a stent may allow for a relatively rapid release and elution of a pharmaceutically effective dose of a therapeutic agent to a target tissue in approximately 5 minutes or less, 4 minutes or less, 3 minutes or less, 2.5 minutes or less, 2 minutes or less, 1.8 minutes or less, 1.6 minutes or less, 1.4 minutes or less, 1.2 minutes or less, 1 minute or less, 0.9 minutes or less, 0.8 minutes or less, 0.7 minutes or less, 0.6 minutes or less, 0.5 minutes or less, 0.4 minutes or less, 0.3 minutes or less, 0.2 minutes or less, or 0.1 minutes or less.

In other embodiments of a stent disclosed herein, the increased surface area created by the rotational spun coating may increase the bioavailability of the therapeutic agent. In some embodiments, the increased surface area of the rotational spun coating may provide for a more efficient release of the therapeutic agent to the tissue. In an embodiment, the increased surface area may allow for a reduction in the amount of therapeutic agent that is used to deliver a pharmaceutically effective dose.

In certain embodiments of the stents disclosed herein, the surface area of the rotational spun coating may be adjusted by increasing or decreasing the density or fiber size of the rotational spun material on the stent. In other embodiments, the stent may be coated with one or more layers of a rotational spun material wherein the various layers may be in different orientations relative to each other. In some embodiments, the surface area of the rotational spun coating on the stent may be adjusted in order to control the delivery of a therapeutic agent.

In further embodiments of the stents disclosed herein, the drug-eluting rotational spun coating may be configured to provide a controlled release of a therapeutic agent to a target tissue. In certain such embodiments, the stent may be coated with one or more layers of a drug-eluting rotational spun material, wherein the one or more layers of the drug-eluting rotational spun material are configured to control the release of the therapeutic agent over a desired period of time while the stent is in place.

For example, in an embodiment, the one or more layers of rotational spun materials may comprise alternating layers of drug-eluting rotational spun material with non-drug-eluting rotational spun material. In other such embodiments, the stent may be coated with one or more layers of a drug-eluting rotational spun material wherein the one or more layers of the drug-eluting rotational spun material are covered with one or more additional controlled release layers that are configured to control the release of the therapeutic agent from the stent. In further embodiments, the stent may be coated with one or more layers of a biodegradable and/or bioabsorbable drug-eluting rotational spun material that may be configured to control the release of the therapeutic agent into the target tissue. In such further embodiments, the stent may be coated with one or more layers of a biodegradable and/or bioabsorbable drug-eluting rotational spun material configured to control the release of the therapeutic agent, and is selected from at least one of chitin, chitosan, collagen, fibrin, and cellulose.

In some embodiments of the stents disclosed herein comprising a drug-eluting rotational spun coating, the rotational spun material may be configured to provide an immediate release or a delayed release of a therapeutic agent. In certain embodiments of a stent coating, the drug-eluting rotational spun material may be configured to release a dose of a therapeutic agent of between about 100 µg and about 600 µg over a desired period of time.

In certain embodiments, the medical devices comprising a drug-eluting rotational spun coating is selected from at least one of a balloon, a stent, a catheter or a vascular graft.

Figure 1B:
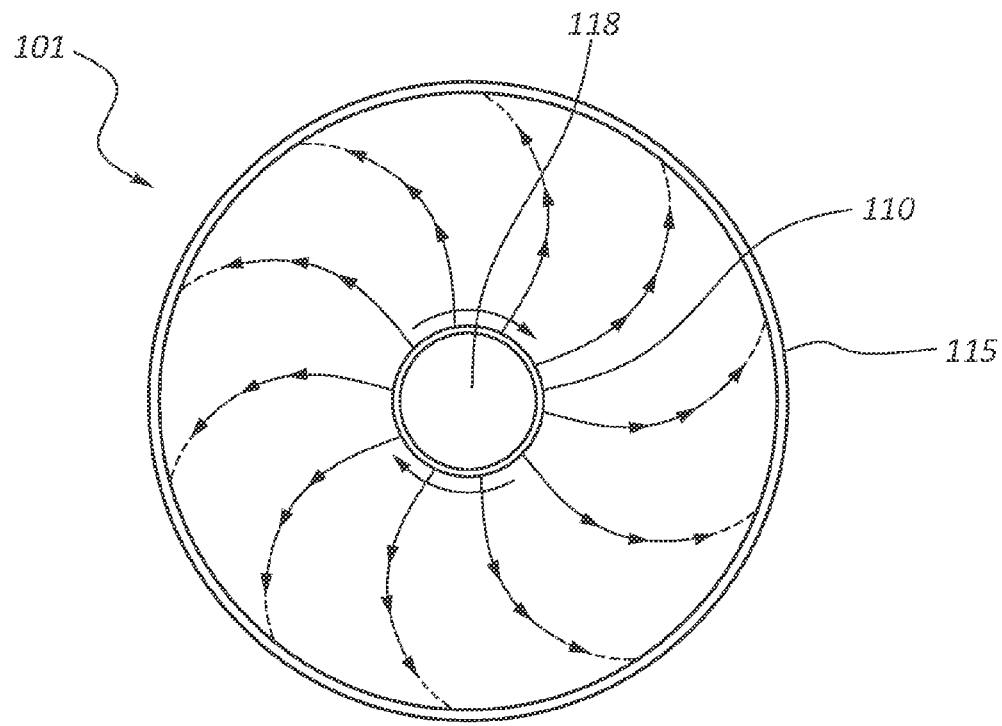
FIG. 1B is a top view of the rotational spinning apparatus of FIG. 1A.
Figure 2A:
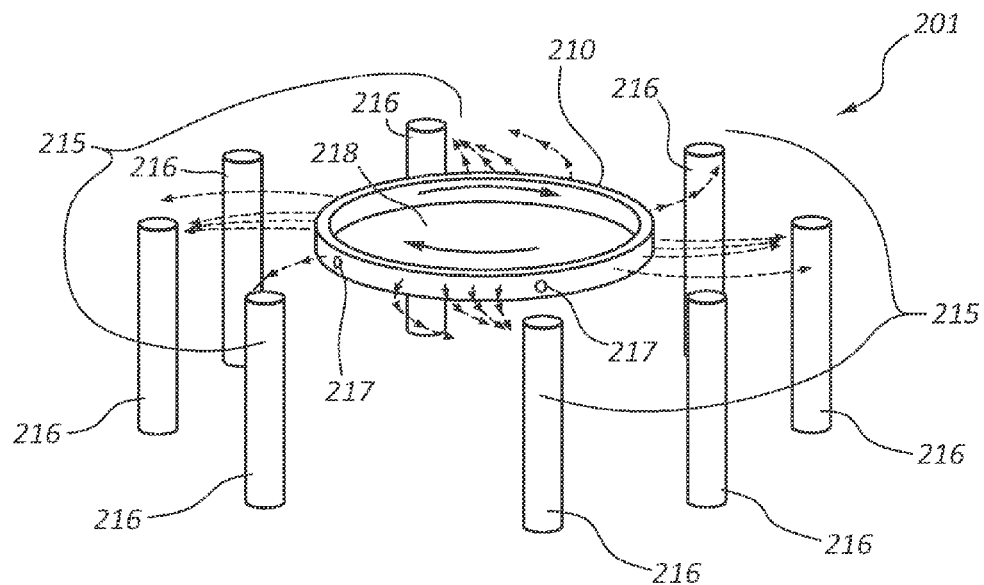
FIG. 2A is a perspective view of another embodiment of a rotational spinning apparatus.
Figure 2B:
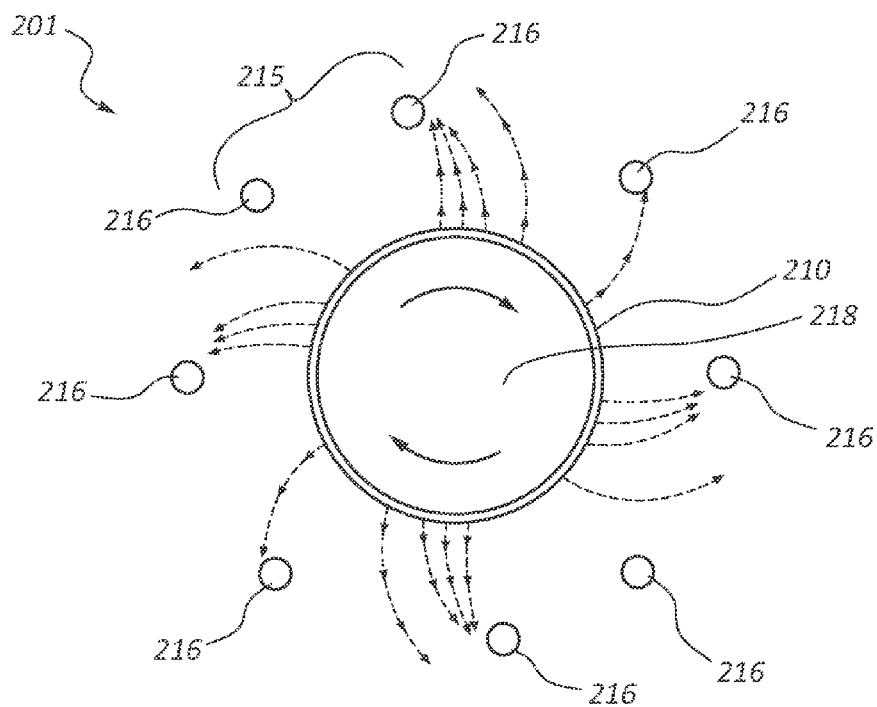
FIG. 2B is a top view of the rotational spinning apparatus of FIG. 2A.

FIG. 1A illustrates an embodiment of a rotational spinning apparatus 101. This Figure, as well as FIGS. 1B, 2A, and 2B, is intended to schematically illustrate the operation of a rotational spinning apparatus, and is not meant to limit the particular structure, shape, or arrangement of rotational spinning apparatus components within the scope of this disclosure. The illustrated apparatus 101 comprises a spinneret 110 disposed near the center of a generally circular collector 115. In the illustrated embodiment the collector 115 forms a ring around the spinneret 110. The spinneret 110 further comprises orifices 117 located around the circumference of the spinneret 110 and a reservoir 118.

The apparatus 101 may be utilized to create a structure of rotational spun fibers deposited on the collector 115. In some embodiments, the collector 115 may be configured such that structures such as rods, tubes, mats, or spheres of rotational spun fibers are created.

In some embodiments, the apparatus 101 may be utilized to create a structure of rotational spun fibers by first filling the reservoir 118 with a flowable material. In certain embodiments, polymeric dispersions, such as an aqueous dispersion, may be used. In further embodiments, the flowable material, which includes for example, polymeric dispersions, aqueous dispersions and polymer solutions, may comprise a therapeutic agent associated with the flowable material during the creation of the rotational spun fibers. In particular embodiments, the flowable material may be mixed with a therapeutic agent selected from a bismuth-containing compound, paclitaxel, rapamycin, heparin, beta-lapachone, and vitamin D. The spinneret 110 may then be rotated such that the flowable material is forced out of the orifices 117 as illustrated by the arrows in FIG. 1A. Molecules, such as polymer chains, may tend to disentangle and/or align as the flowable material is forced through the orifice. Additionally, in some embodiments, the orifice 117 comprises a needle or nozzle that extends from the outside circumference of the spinneret 110. Still further, in some embodiments, the orifice 117 may comprise a cannula configured with a quick connection, such as a luer connection, which allows for the rapid exchange of various cannula sizes.

As the flowable material is expelled from the reservoir 118, drag or other aerodynamic forces acting on the stream or jet of expelled material may cause the material to elongate and bend, forming a relatively small diameter fiber of material. In some instances drag may be a shear force with respect to the stream. Additionally, certain components of the flowable material, such as the material medium or solvent, may partially or fully evaporate as the material is drawn into fibers. In certain embodiments utilizing flowable materials which do not contain a solvent, such as molten material, there may be no evaporation as the material is drawn into fibers. In further embodiments, flowable materials which do not contain a solvent, such as molten material, may experience convection cooling that may influence fiber diameters.

In some embodiments, the material supplied to the reservoir 118 may be continuously supplied (for example by a feed line), including embodiments where the reservoir is pressurized or supplied by a pressurized source. Further, in certain embodiments, the material may be heated near or above its melting point prior to rotational spinning, including embodiments wherein the material is melted and not dispersed in a solvent. Thus, in some embodiments, rotational spinning molten material does not include the use of solvents; therefore there is no need to remove solvent from the deposited material, such as a mat, at a later step in the process. In some instances the material may be supplied to the reservoir as pellets which are heated and melted within the reservoir.

In certain embodiments, the fibers eventually contact, and are deposited on, the collector 115. The combination of forces described herein may interact as the fibers are deposited, causing the fibers to be disposed in random patterns on the collector 115. In some embodiments, air currents may be introduced through, for example, the use of fans, to partially control the deposition of the fibers on the collector 115.

Still further, in some instances the collector 115 may have an electrostatic charge. Additionally, in some embodiments, rotational spun structures may be combined with electrospun structures, including embodiments where some layers of material are rotational spun and some are electrospun, but both are deposited on the same substrate.

In some embodiments utilizing certain flowable materials, the deposited fibers are removed from a substrate, such as the collector 115, and sintered, or sintered then removed. For example, sintering may occur after the deposition of PTFE fibers, including PTFE fibers spun from a dispersion. The sintering process may set or bond the structure of the rotational spun fibers and remove any remaining dispersion medium or solvent. In some embodiments, the fibers are not sintered and are self-curing rotational spun fibers. In certain such embodiments, the fibers may include self-curing rotational spun fibers comprising nylon 6.

In some embodiments, the structure may be treated at a first temperature to remove solvents and a second temperature to sinter the deposited material. For example, a PTFE structure spun from an aqueous dispersion may be first treated at a temperature below the sintering temperature of PTFE in order to remove any remaining water. For example, the rotational spun structure may be heated to about 200° C. to remove any remaining water in the structure. Further, other materials such as cosolvents or fiberizing agents may be evaporated or otherwise removed at this stage. In some embodiments, as further detailed herein, an aqueous PTFE dispersion may be mixed with polyethylene oxide (PEO) prior to rotational spinning of the material. Treating the spun structure at temperatures such as 200° C. may remove excess or unreacted PEO in addition to the water. In some embodiments, the PTFE structure may then be sintered at about 385° C. In other embodiments, PTFE sintering may be completed at temperatures from about 360° C. to about 400° C., and/or at temperatures in excess of the crystalline melt point of the PTFE (about 342° C.). In some embodiments, the structure may be heated only to the sintering temperature, removing any remaining solvent and/or PEO while simultaneously sintering the deposited PTFE material. Additionally or alternatively, in certain embodiments, solvents or other materials may be removed by rinsing the deposited rotational spun material.

Sintering may set the structure of the rotational spun material even if the temperature at which the material is sintered is not sufficient to cause cross linking of the polymer chains. PTFE sintering may create solid, void free, PTFE fibers.

FIG. 1B is a top view of the rotational spinning apparatus 101 of FIG. 1A, illustrating the spinneret 110, the collector 115, and the reservoir 118. In the illustration of FIG. 1B, potential arced paths of the streams of material interacting with drag forces are illustrated by arrows and dotted lines. These lines are exemplary and not intended to reflect the precise path of the fibers. In certain embodiments, the fibers may loop completely around the spinneret 110 before contacting the collector 115, including embodiments where the fiber path encircles the spinneret 110 more than one time before contacting the collector 115.

The distance between the spinneret 110 and the collector 115 may impact the diameter of the deposited fibers. In some embodiments, the longer the fibers are drawn out before contacting the collector 115, the smaller the resulting fiber diameters. Similarly, smaller distances between the spinneret 110 and the collector 115 may be configured to produce larger diameter fibers.

Processes such as the exemplary process described herein may be utilized to create rotational spun fiber coatings comprised of small diameter fibers, including microfibers and/or nanofibers. As used herein, a small diameter fiber is less than 750 nanometers in diameter, a medium diameter fiber is between 750 nanometers and 2 microns in diameter, and a large diameter fiber is at least 2 microns and up to 1 millimeter in diameter. The rotational spun fibers may be incorporated into a medical device, such as a balloon or a stent, configured for implantation in the human body. In certain embodiments, the nanofiber or microfiber coatings may be configured to permit tissue ingrowth and/or endothelial growth or attachment on the rotational spun fibers. For example, the rotational spun structure may be configured to contain openings within or between the deposited fibers configured to permit interaction with tissue and/or cells. As further detailed herein, the percent porosity of a fiber structure, the thickness of the structure, and the diameter of the fibers comprising the structure may each be configured to create a fiber structure with desired properties, including rotational spun coatings that tend to permit or resist tissue ingrowth and/or endothelial growth or attachment.

Multiple variables may be controlled to affect the properties of a rotational spun structure, including, for example, the rotational speed of the spinneret; the viscosity of the flowable material; the temperature of the spinneret; introduced air currents; and the thickness of the deposited material. In some embodiments with fibers spun from molten material, the melt flow index (MFI) of the material may also impact the nature of the spun mat. In some embodiments, materials with an MFI of from about 1 g/10 min to about 5000 g/10 min, including from about 200 g/10 min to about 1500 g/10 min and from about 10 g/10 min to about 30 g/10 min, will tend to form fibers when spun.

In other embodiments, a rotational spun structure or mat may be configured to resist tissue ingrowth into or through the mat. In such embodiments, the mat may be configured with very small pores, or essentially no pores at all, thus preventing tissue ingrowth into or through the mat. In certain embodiments, a medical device may be constructed partially of rotational spun materials configured to permit tissue ingrowth and/or endothelial growth or attachment, and partially of rotational spun materials configured to resist tissue ingrowth and/or attachment. Characteristics of the rotational spun fiber mat, such as porosity and average pore size, may be controlled during the rotational spinning process to create certain coatings which permit tissue ingrowth and/or endothelial growth or attachment. In certain embodiments, characteristics of the coating may be controlled to create coatings which resist or are impermeable to tissue ingrowth and/or attachment.

A variety of materials may be rotational spun to form structures and coatings for medical devices such as balloons and stents. Exemplary materials which may be rotational spun for use in medical devices include PTFE, polyamides (including nylon), fluorinated ethylene propylene (FEP), Dacron or polyethylene teraphthalate (PET), Kevlar, polyurethanes, polycarbonate, polypropylene, Pebax, polyethylene, aromatic polyimides, biological polymers (such as collagen, chitin, chitosan, fibrin, and elastin), and ceramics.

Furthermore, therapeutic agents may be associated with the rotational spun coatings. For example, in an embodiment, a therapeutic agent is added directly to the flowable material used to rotationally spin the coating. Exemplary therapeutic agents include radiopaque materials such as bismuth-containing compounds, antimicrobial agents such as silver sulfadiazine, antiseptics such as chlorhexidine or silver, and anticoagulants such as heparin. In certain embodiments, bismuth-containing compounds may exhibit one or more therapeutic effects such as increasing endothelial attachment, antimicrobial properties, anticancer properties, and anti-fungal properties. In some embodiments, bismuth-containing compounds may increase the strength and durability of the rotational spun coating. In some embodiments, bismuth-containing compounds may be used to control the porosity and microstructural properties of a rotational spun material or device.

Exemplary bismuth-containing compounds include bismuth salts, bismuth nitrate, bismuth oxide, or bismuth subsalicylate. In some embodiments, the bismuth-containing compound is associated with the rotational spun coatings described herein. In some embodiments, the bismuth-containing compound is applied to the rotational spun materials described herein. In certain embodiments, the bismuth-containing compound is heated past its melting point and rotationally spun and used as a coating applied to other rotational spun materials or as a coating on medical devices. In some further embodiments, a bismuth-containing compound may be applied to the rotational spun coatings described herein by melting, spraying, dipping or rolling.

In particular embodiments, bioabsorbable therapeutic agents may be associated with rotational spun coatings, including fibrin, chitin, chitosan and/or collagen. In some embodiments, a layer of at least one therapeutic agent may be added to a rotational spun coating during manufacture. Additionally, some devices may be constructed with more than one therapeutic agent, including for example, embodiments wherein a medical device is comprised of alternating layers of materials which each contain a different therapeutic agent. Moreover, in some embodiments, a medical device may consist of one or more layers of rotational spun materials configured to control the release of a therapeutic agent, or of a layer containing a therapeutic agent disposed between or next to layers which do not contain a therapeutic agent. Layers which contain a therapeutic agent may be configured to reduce or otherwise modify or influence the biological response of the body to the implantation of a medical device. In certain embodiments, a medical device may comprise one or more layers of rotational spun materials that are subsequently sprayed, brushed, painted or otherwise coated with a therapeutic agent. In some embodiments, a medical device comprising one or more layers of rotational spun materials is dipped into a therapeutic agent.

Referring specifically to FIGS. 2A and 2B, another schematic embodiment of a rotational spinning apparatus 201 is illustrated. FIGS. 2A and 2B illustrate an apparatus analogous to that shown in FIGS. 1A and 1B. It will be appreciated by one of skill in the art having the benefit of this disclosure, that analogous components of the two apparatuses may be interchangeable and that disclosure provided in connection with each embodiment may be applicable to the other, and vice versa.

FIG. 2A is a perspective view of the rotational spinning apparatus 201 while FIG. 2B is a top view of the same. The rotational spinning apparatus 201 includes a spinneret 210 comprising a reservoir 218 and orifices 217. As compared to the apparatus 101 of FIGS. 1A and 1B, in the embodiment of FIGS. 2A and 2B the collector 115 is configured as a plurality of cylindrical mandrels 216. Thus in FIGS. 2A and 2B, the plurality of mandrels 216 are collectively designated as a collector 215, but individually designated by the numeral 216. The term "collector" as used in connection with FIGS. 1A-2B, and indicated by numerals 115 and 215, is intended to broadly refer to any collection device or apparatus without defining a particular size, shape, or orientation. For example, in some embodiments, the collector may be configured as a ring, such as the collector 115 illustrated in FIGS. 1A and 1B. In other embodiments the collector 215 may be a plurality of cylinders as shown in FIGS. 2A and 2B. In still other embodiments, the collector may comprise a rotating belt (not shown), configured to facilitate rotational spinning of a continuous sheet of material. In further embodiments, the collector may comprise a medical device, such as a balloon or a stent.

Embodiments configured to form a continuous sheet of rotational spun material may be configured to produce mats, including mats from about one meter to about 9 meters in width, including mats of about 3 meters in width. Also, mats from about one foot wide to about one meter wide (as well as larger or smaller mats) may be formed. In some instances, a sintering oven may be positioned such that as the mat moves away from the spinneret (for example, on a rotating belt), the mat enters an oven and is sintered. The sintered mat may then be collected onto a spool. Further, in some embodiments, the entire spool may then be cut into smaller widths, forming strips of rotational spun material. For example, strips from about 0.1 inch wide to about 2 inches wide may be formed. Such strips may be utilized for the construction of tubular medical devices by wrapping the strips around a mandrel. The strips may overlap and/or may be wound such that the tube formed does not have a distinct seam along the length of the tube. In certain embodiments, the mat may be wound in multiple layers around the mandrel. Further, the mat formed may be relatively thin, or film-like. The thickness of the coating formed on the mandrel (and other characteristics such as porosity) may be controlled, for example, by the number of layers of film wound onto the mandrel.

In embodiments wherein the rotational spun material is formed of PTFE, the sintering temperature may be from about 360° C. to about 400° C., including temperatures of about 385° C. or temperatures above the crystalline melting temperature of the PTFE, or about 342° C. Similarly, for other materials, sintering may be done at or above the crystalline melting temperature of other spun material. Again, either prior to or as part of the sintering process, heat treating may be configured to remove PEO and/or solvent, in instances where the PTFE or other polymer was combined with such elements prior to spinning the mat. In other embodiments, the rotational spun material may be a self-curing material that does not require sintering or heating to cure.

In the embodiment of FIGS. 2A and 2B, the mandrels 216 may be disposed about the spinneret 210 in a generally circular configuration. In some embodiments, the mandrels 216 may be stationary, while in other embodiments the mandrels 216 may be configured to rotate about their axes. In some embodiments the mandrels 216 may each be driven by the same belt, allowing each to maintain the same rotational speed. In other embodiments, some or all of the mandrels 216 may be independently driven.

In the illustrated embodiment, the mandrels 216 are disposed vertically, or such that the axis of each mandrel is substantially parallel to the axis of rotation of the spinneret. In such embodiments, the vertical mandrels 216 may be used to support a medical device, such as a balloon or a stent, parallel to the axis of rotation of the spinneret. In another exemplary embodiment, one or more of the mandrels 216 may be disposed horizontally, or such that the axis of those mandrels is substantially orthogonal to the axis of rotation of the spinneret. In such embodiments, the horizontal mandrels 216 may be used to support a medical device, such as a balloon or a stent, substantially orthogonal to the axis of rotation of the spinneret. In some embodiments, the axis of the mandrel 216 may be generally parallel to the axes of fibers being spun. Horizontally disposed mandrels 216 may be configured to produce mats having generally less fiber alignment than vertical mandrels. Horizontal mandrels may further be configured to produce mats with relatively uniform thickness around the mandrel.

In addition to horizontal mandrels, further embodiments may comprise mandrels disposed in any relative position with respect to the axis of the spinneret. Mandrels mounted in any disposition may be configured as stationary collection devices, or may be configured to rotate. Additionally, combinations of mandrels in a variety of positions may be used simultaneously. Furthermore, in some embodiments one or more mandrels 216 may be configured for use in connection with a vacuum system. For example, openings in the surface of the mandrel, such as micro-porous mandrels 216, may tend to draw fibers toward the mandrel in instances where the interior of the mandrel 216 has lower pressure than the exterior of the mandrel 216.

In embodiments wherein the mandrels 216 rotate, the spinning motion of each mandrel 216 may tend to deposit the fibers around the entire surface of the mandrel. Thus, as the fibers are deposited on each mandrel 216, a seamless tube of fiber material, such as microfiber or nanofiber material, may form on each mandrel 216. The density of the fibers, the thickness of the mat, and other characteristics may be controlled by multiple variables, including the distance from the spinneret 210 to the mandrels 216, the rotational speed of the spinneret 210, the rotational speed of the mandrels 216, the orientation of the mandrels 216, and the characteristics of the flowable material being spun.

In some embodiments, mats of rotational spun material formed on a spinning mandrel 216 may thus comprise a tubular membrane having no seam and substantially isotropic properties. In certain embodiments, the collection mandrel 216 may rotate at rates between about 1 RPM and about 2000 RPM during the rotational spinning process, including rates from about 1000 RPM to about 1500 RPM, including about 1500 RPM, or about 50 RPM to about 300 RPM, including about 150 RPM. In other embodiments, the collection mandrel 216 may rotate at rates between about 1 RPM and about 10,000 RPM during the rotational spinning process, including rates from about 2,500-7,500 RPM or about 5,000 RPM.

Furthermore, controlling the rotational speed of the mandrels 216 may influence both the density of the mat formed on the mandrels 216 and the general alignment of fibers in the mat. For instance, in some embodiments utilizing vertical mandrels, the faster the mandrel 216 is spinning, the more the fibers may tend to be deposited in-line with other fibers. For example, the aligned fibers may be produced by rotating the collection mandrel 216 at rates ranging from between about 2,000 RPM to about 10,000 RPM during the rotational spinning process. In some examples, the rotationally spun fibers may be spun at approximately 2,000 to 3,000 RPM, 2,000 to 3,500 RPM, 3,000 to 4,000 RPM, 3,000 to 5,000 RPM, 4,000 to 5,000 RPM, 5,000 to 6,000 RPM, 6,000 to 7,000 RPM, 7,000 to 8,000 RPM, 8,000 to 9,000 RPM, and 9,000 to 10,000 RPM. Further, the relative density of the fibers, for example, as measured by percent porosity, may be controlled in part by the rotational speed of the mandrels 216. FIGS. 9A-10B are SEMs of exemplary mats rotational spun onto rotating mandrels.

In some embodiments, a medical device comprising a scaffolding structure, such as a stent wire, may also be on the mandrel 216, and the fibers are rotationally spun directly onto the mandrel 216 and scaffolding structure. In other embodiments, a medical device comprising a balloon or balloon catheter may be on the mandrel 216, wherein a rotational spun coating is spun directly onto the balloon or balloon catheter.

Coatings composed of rotational spun materials may have a microstructure composed of many fibers crossing each other at various and random points. The rotational spinning process may control the thickness of this structure and thereby, the relative permeability of the mat. As more and more fibers are rotationally spun onto a mat, the mat may both increase in thickness and decrease in permeability (due to successive layers of strands occluding the pores and openings of layers below). Certain details of this microstructure are shown in FIGS. 7A-21, which are discussed in more detail herein.

In certain embodiments, the rotational spun coatings or mats produced in connection with the present disclosure may be described by general parameters selected from at least one of therapeutic agent content, percent porosity, mat thickness, and fiber diameter. Each of these parameters may impact the nature of the mat, including the bioavailability of the therapeutic agent, the delivery rate of the therapeutic agent, the tendency of the coating to permit tissue ingrowth and/or endothelial attachment or the tendency of the coating to resist tissue ingrowth or endothelial attachment. Each of these parameters may be optimized with respect to each other to create a rotational spun coating having particular characteristics.

Percent porosity refers to the percent of open space to closed space (or space filled by fibers) in a fiber mat. Thus, the more open the mat is, the higher the percent porosity measurement may be. In some instances, percent porosity may be determined by first obtaining an image, such as an SEM, of a rotational spun material. The image may then be converted to a "binary image," or an image showing only black and white portions, for example. The binary image may then be analyzed and the percent porosity determined by comparing the relative numbers of each type of binary pixel. For example, an image may be converted to a black and white image wherein black portions represent gaps or holes in the rotational spun mat while white portions represent the fibers of the mat. Percent porosity may then be determined by dividing the number of black pixels by the number of total pixels in the image. In some instances, a code or script may be configured to make these analyses and calculations.

In some embodiments, percent porosities from about 30% to about 80% may be configured to permit tissue ingrowth into the layer and/or permit endothelial growth or attachment on the layer, including mats of about 40% to about 60%, or mats of about 50% porosity. Less open layers may be configured to resist such ingrowth and/or attachment. Because the fibers comprising the mat are deposited in successive layers, the second parameter, mat thickness, may be related to porosity. In other words, the thicker the mat, the more layers of fibers, and the less porous the mat may be. In some embodiments, mats from about 20 micrometers to about 100 micrometers in thickness may be configured for use in connection with the present disclosure, including mats from about 40 micrometers to about 80 micrometers.

Fiber diameter may be a measurement of the average fiber diameter of a sample in some instances. In some embodiments, fiber diameters from about 50 nanometers to about 3 micrometers may be used in connection with the present disclosure. In certain embodiments, the drug-eluting rotational spun coating comprises rotational spun fibers approximately one micron in diameter or smaller. In other embodiments, the drug-eluting rotational spun coating comprises rotational spun fibers between approximately one millimeter and one micron in diameter. Notwithstanding these or other specific ranges included herein, it is within the scope of this disclosure to configure a mat with any combination of values for the given parameters.

In some embodiments the "average pore size" of the mat may be used as an alternate or additional measurement of the properties of the mat. Average pore size can be indirectly determined by measuring the permeability of the mat to fluids using known testing techniques and instruments. Once the permeability is determined, that measurement may be used to determine an "effective" pore size of the rotational spun material. As used herein, the "pore size" of a rotational spun material refers to the pore size of a membrane which corresponds to the permeability of the rotational spun material when measured using ASTM standard F316 for the permeability measurement. This standard is described in ASTM publication F316 "Standard Test Methods for Pore Size Characteristics of Membrane Filters by Bubble Point and Mean Flow Pore Test," which is incorporated herein by reference. In some instances, this test can be used as a quality control after configuring a rotational spun material based on the three parameters (percent porosity, thickness, and fiber diameter) discussed herein.

Figure 3A:
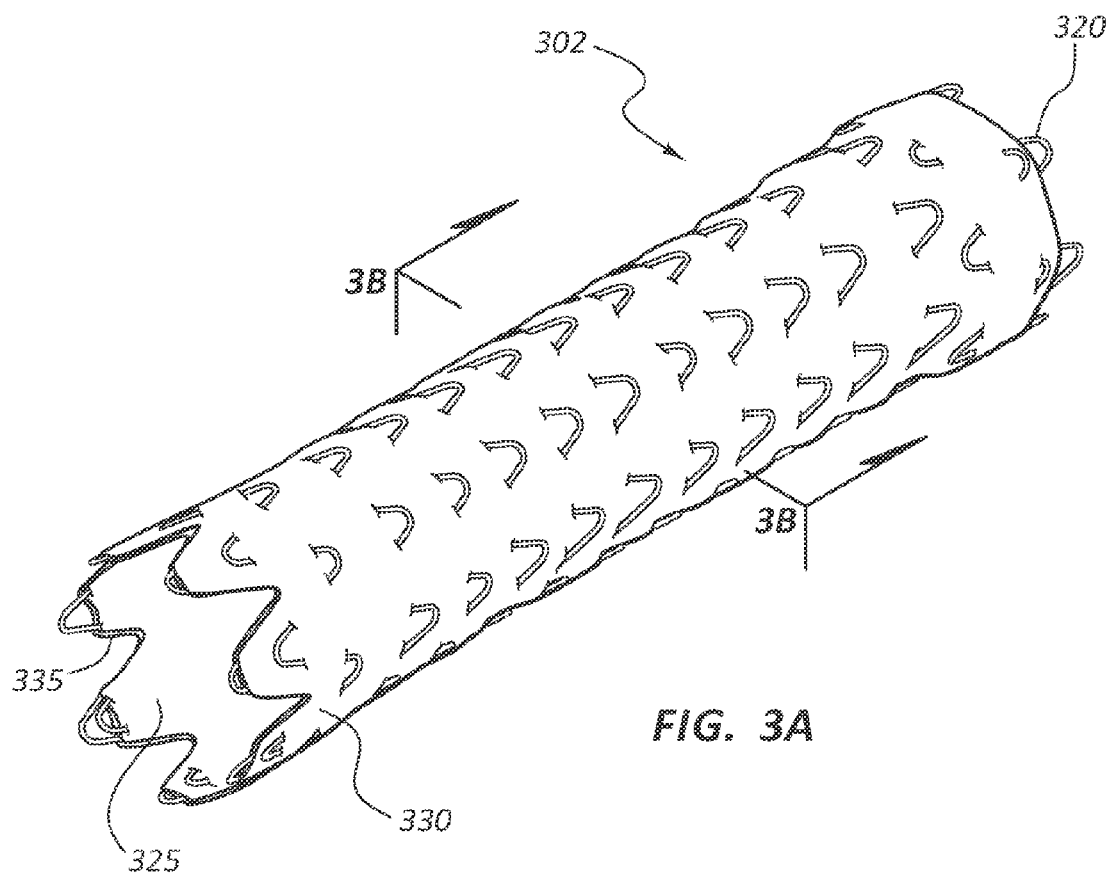
FIG. 3A is a perspective view of a coated stent.
Figure 3B:
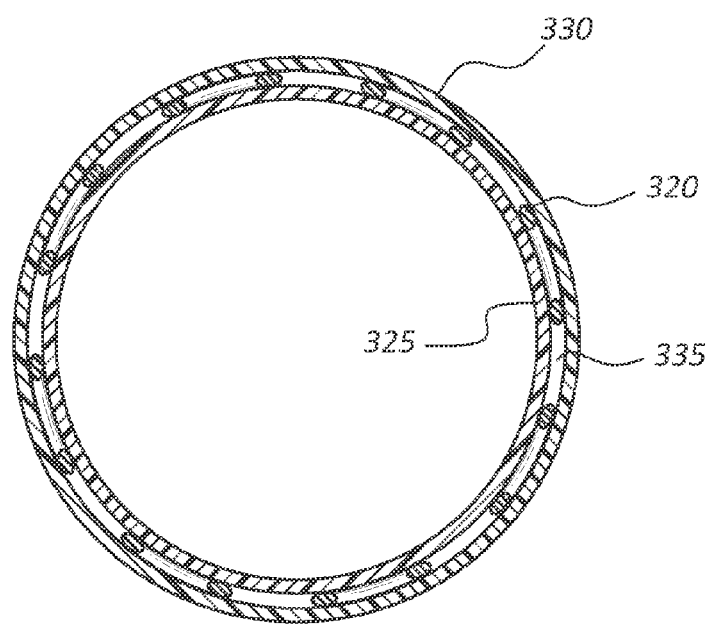
FIG. 3B is a cross sectional view of the coated stent of FIG. 3A taken through line 3B-3B.

FIGS. 3A and 3B illustrate an exemplary medical device comprising a stent 302. The stent 302 comprises a scaffolding structure 320 and a coating comprising a drug-eluting rotational spun outer layer 330, an optional inner layer 325, and an optional tie layer 335. In other embodiments, a stent coating may have more or fewer layers than the illustrated embodiment, including embodiments with only one coating layer.

In some applications, it may be desirable to create a medical appliance such as stent 302 with a drug-eluting rotational spun outer layer 330 comprising a therapeutic agent which may decrease the incidence of lumen tissue surrounding the stent, growing into or attaching to the stent. This may be desirable in applications where the stent is used to treat stenosis or other occlusions; an outer layer may prevent tissue from growing into or through the material toward or into the lumen of the stent and reblocking or restricting the body lumen. In some embodiments, a substantially impermeable outer layer may be produced by using rotational spun material with a percent porosity from about 0% to about 50%, including about 25%; a thickness from about 20 micrometers to about 100 micrometers, including from about 40 micrometers to about 80 micrometers; and fiber diameters from about 50 nanometers to about 3 micrometers.

Additionally or alternatively, a substantially impermeable mat may have an average pore size of about 0 microns to about 1.5 microns. In other embodiments, the impermeable layer may have an average pore size of less than about 0.5 micron. In yet other embodiments, the impermeable layer may have an average pore size of less than about 1 micron. In some embodiments, the impermeable layer may be a layer other than the outer layer, such as a tie layer, an intermediate layer, or an inner layer.

In certain embodiments, a medical device such as stent 302 may be coated with a drug-eluting rotational spun inner layer 325 and/or a drug-eluting rotational spun outer layer 330. In one such embodiment, the outer layer 330 may comprise a therapeutic agent and be configured to be substantially impermeable to tissue ingrowth and/or attachment.

Similarly, in other potential embodiments, it may be desirable to create a medical device such as stent 302 with a drug-eluting rotational spun outer layer 330 which is porous. A porous outer layer 330 may permit healing and the integration of the prosthesis into the body. For instance, tissue of the surrounding lumen may grow into the porous outer diameter or attach to the outer diameter layer. This tissue ingrowth may permit, modulate, and/or influence healing at the therapy site. In some embodiments, a porous outer layer 330 may be formed of rotational spun PTFE.

In certain embodiments, a relatively porous inner layer 325 may be desirable. This layer may or may not be used in conjunction with a substantially impermeable outer layer 330. In other embodiments, inner layer 325 may comprise a relatively porous drug-eluting rotational spun layer. A relatively porous inner layer may permit tissue ingrowth and/or endothelial attachment or growth on the inside diameter of the stent 302 which may be desirable for any combination of the following: healing, biocompatibility, prevention of thrombosis, or reducing turbulent blood flow within the stent. In some embodiments, the inner layer may be comprised of a mat, such as a rotational spun PTFE mat, having a percent porosity of about 40% to about 80%, including about 50%; a thickness of about 20 micrometers to about 100 micrometers, including from about 40 micrometers to about 80 micrometers; and fiber diameters from about 50 nanometers to about 3 micrometers. Additionally or alternatively, the mat may be comprised of a rotational spun mat, such as PTFE, with an average pore size of about 1 micron to about 12 microns, such as from about 2 microns to about 8 microns, or from about 3 microns to about 5 microns, or alternatively from about 3.5 microns to about 4.5 microns.

FIGS. 4A-4E illustrate certain steps in a process of manufacturing a multilayer construct for use in connection with a medical device. More specifically, these figures illustrate a process of creating a stent coated with a drug-eluting rotational spun material. This disclosure is equally relevant to all medical devices which may comprise a coating or multilayered construct, including grafts such as a vascular graft, patches, and stents.

Figure 4A:
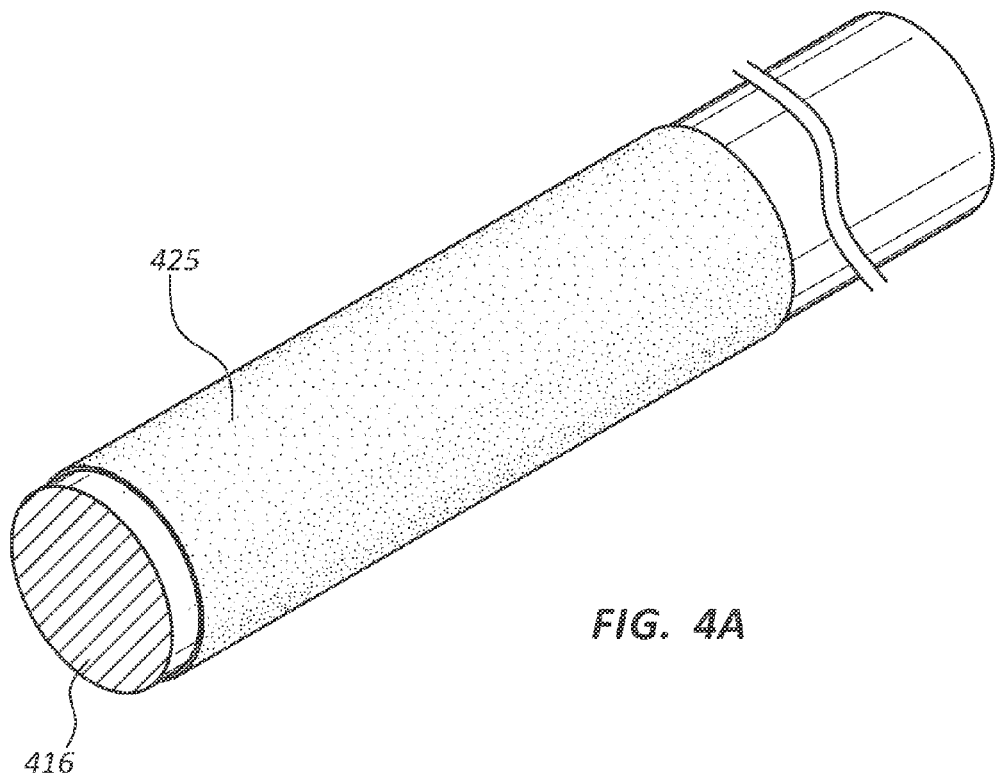
FIG. 4A is a perspective view of a rotational spun coating on a mandrel.

FIG. 4A illustrates a coating inner layer 425 disposed around a mandrel 416. The inner layer 425 may be rotationally spun directly onto the mandrel 416, including instances wherein the mandrel 416 was rotating during the process. In the illustrated embodiment, the inner layer 425 was rotationally spun onto a rotating mandrel 416 such that the resultant tube of material has no seam. After the inner layer 425 is rotationally spun onto the mandrel 416, the inner layer 425 may self-cure or may then be sintered. In the case of PTFE, the membrane may be sintered at temperatures of about 385° C., including temperatures from about 360° C. to about 400° C. Sintering may tend to set the structure of the PTFE, meaning sintering reduces the softness or flowability of the PTFE. Furthermore, as discussed herein, sintering or otherwise heat treating the mat may evaporate any solvent or PEO mixed with the PTFE, resulting in a material comprised substantially of pure PTFE.

Figure 4B:
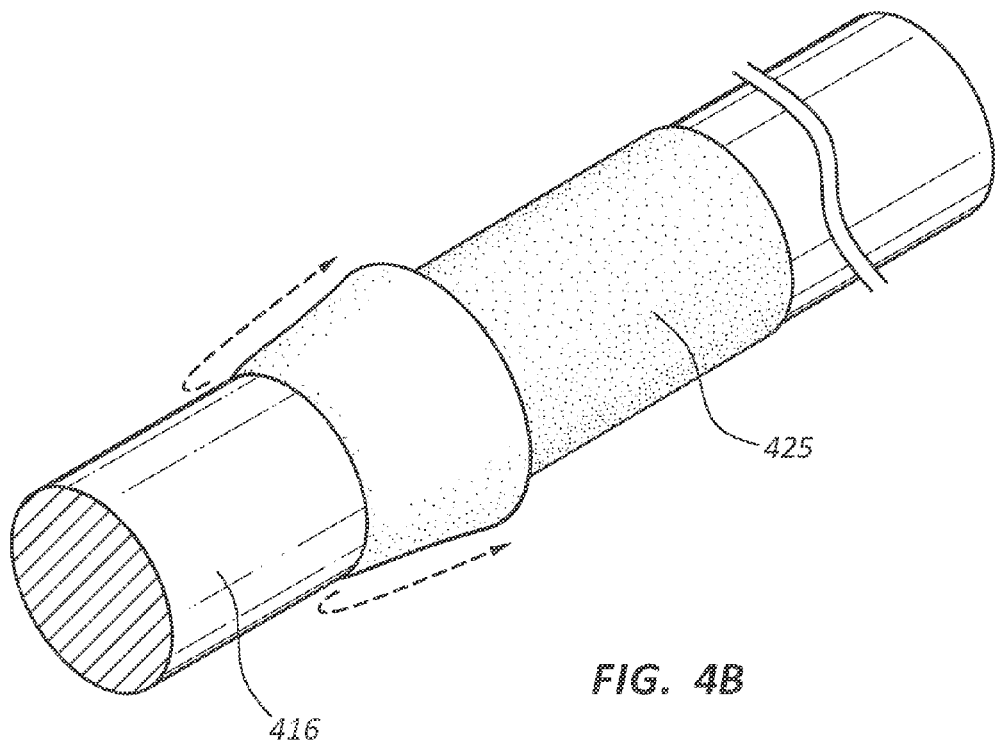
FIG. 4B is a perspective view of the coating of FIG. 4A partially removed from the mandrel.
Figure 4C:
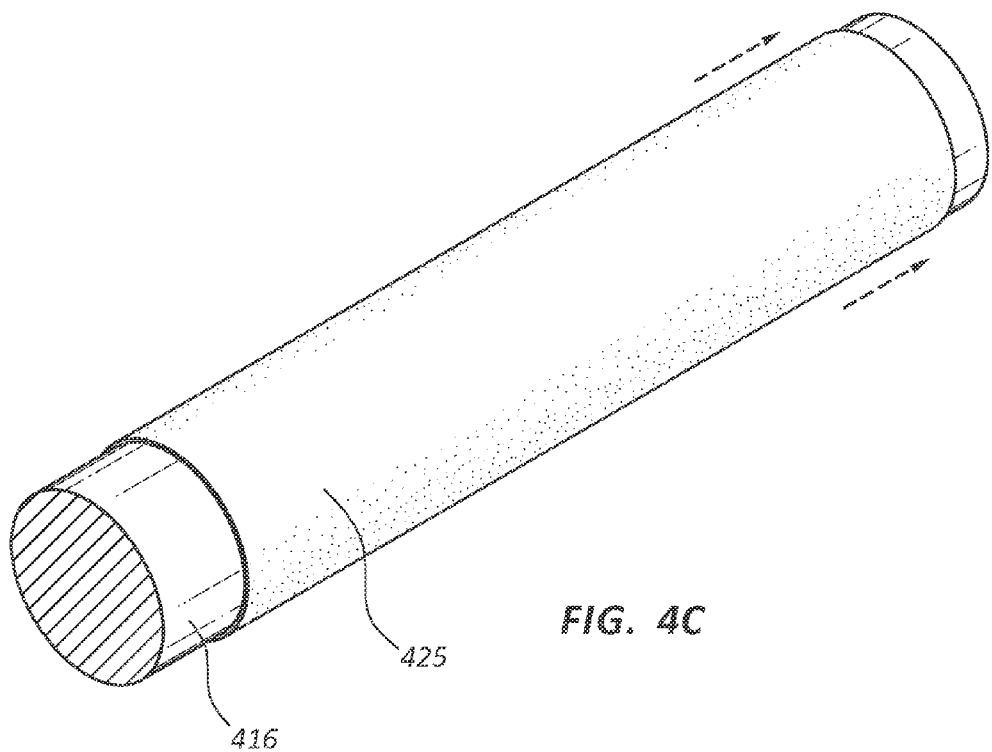
FIG. 4C is a perspective view of the coating of FIG. 4A repositioned on the mandrel.

Once the inner layer 425 is cured, the tube of material may be removed from the mandrel 416, as illustrated in FIG. 4B. As shown in the illustrated embodiment, the inner layer 425 may be "peeled" from the mandrel 416 to initially break any adherence of the inner layer 425 to the mandrel 416. The inner layer 425 may also be removed by pushing the coating with respect to the mandrel 416, causing the material to bunch as it is removed from the mandrel 416. In some embodiments, low friction coatings may alternatively or additionally be applied to the mandrel 416 before the inner layer 425 is rotationally spun. The inner layer 425 may then be reapplied to the mandrel 416, by slipping the inner layer 425 over the mandrel 416, as illustrated in FIG. 4C.

Figure 4D:
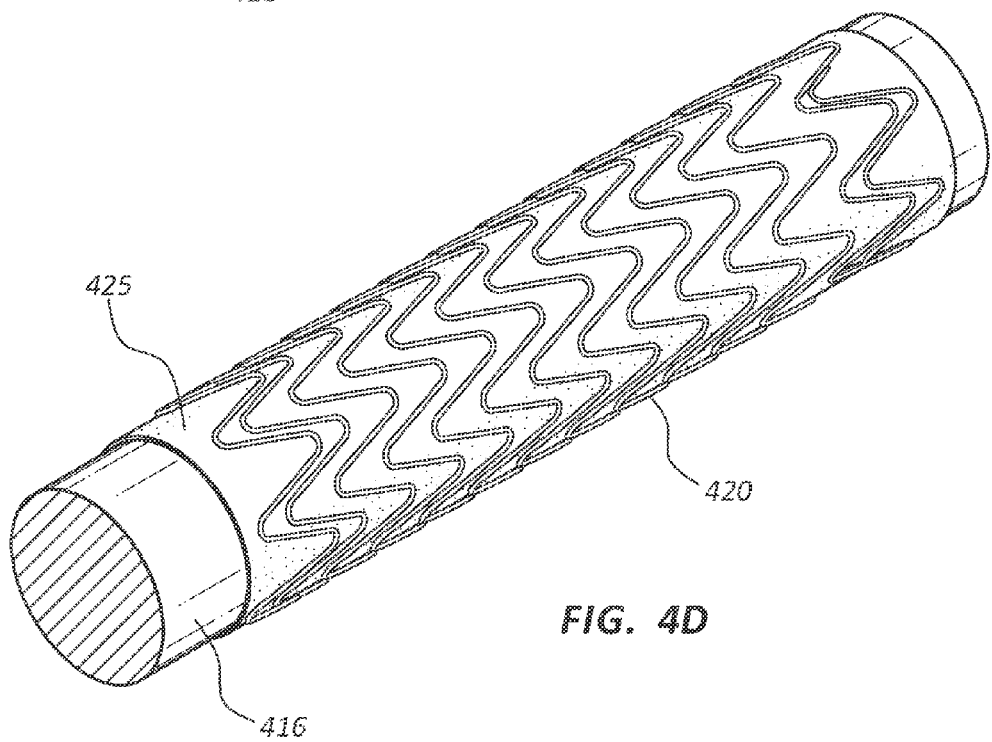
FIG. 4D is a perspective view of a scaffolding structure wound around the coating and mandrel of FIG. 4C.
Figure 4E:
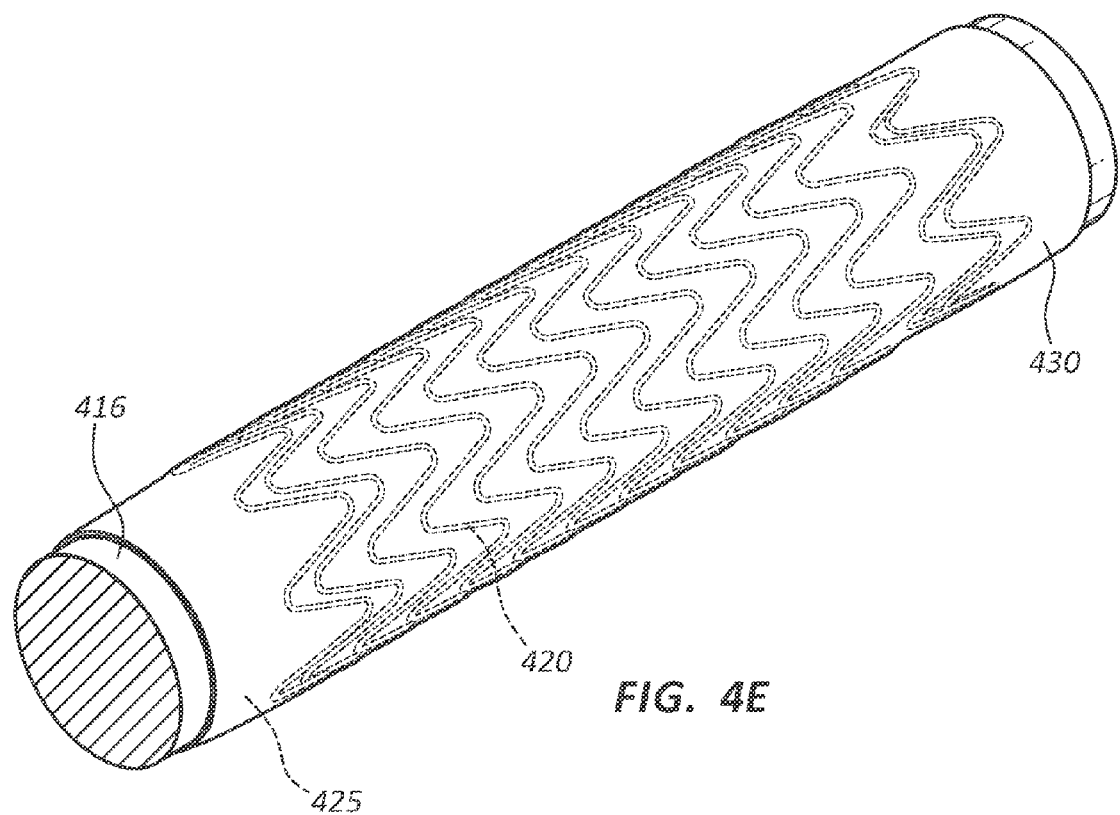
FIG. 4E is a perspective view of the scaffolding structure of FIG. 4D with a second rotational spun coating.

Once the inner layer 425 is reapplied to the mandrel 416, a wire scaffolding 420 can be formed over the mandrel 416 and the inner layer 425, as shown in FIG. 4D. FIG. 4E illustrates an outer layer 430 of material which may then be rotational spun onto the scaffolding 420 and the inner layer 425. Additional layers may also be added through similar processes.

Many variations to the herein-described processes are contemplated and within the scope of the present disclosure. For example, one or more layers may be applied by wrapping strips or mats of material around the mandrel 416 and/or the other layers. Further, some of the layers may be applied by spray or dip coating the mandrel 416 and/or the other layers. In other instances, a therapeutic agent may be applied to one or more of the rotational spun layers by dipping, spraying or coating of the rotational spun layers before and/or after they have cured. In specific embodiments, at least one rotational spun layer may be sprayed with, or dipped into a therapeutic agent. In certain embodiments, the rotational spun layer having an applied therapeutic agent may be at least partially coated with a layer of collagen by, for example, rotational spinning, dipping, or spraying. It is within the scope of this disclosure to vary the processes herein to apply to any of the layers, or any additional layers, using any method disclosed herein.

Figure 5:
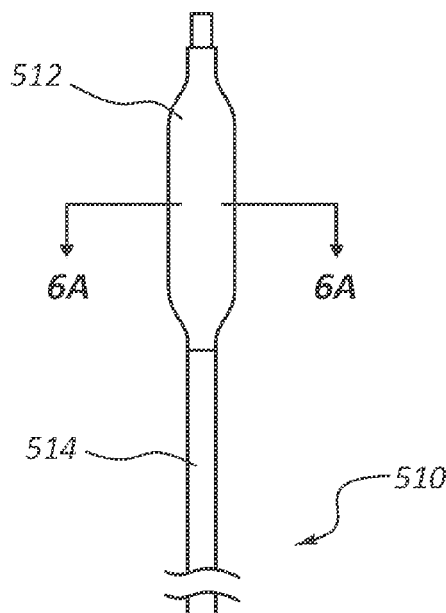
FIG. 5 is a perspective view of one embodiment of a balloon catheter.
Figure 5:
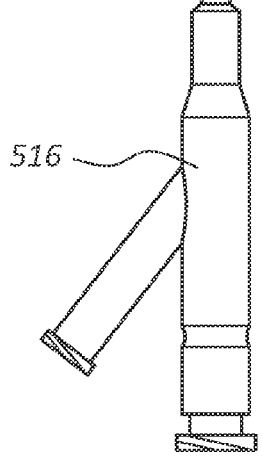

FIG. 5 illustrates an exemplary medical device comprising a balloon catheter 510 having a drug-eluting rotational spun coating on the inflatable balloon 512. Handle assembly 516 may connect to and/or receive one or more suitable medical devices, such as a source of inflation media (e.g., air, saline, or contrast media). Flexible member 514 may be a tube made of suitable biocompatible material and having one or more lumens therein. At least one of the lumens is configured to receive inflation media and pass such media to balloon 512 for its expansion. The balloon catheter 510 may be a rapid exchange or over-the-wire catheter and made of any suitable biocompatible material.

Figure 6A:
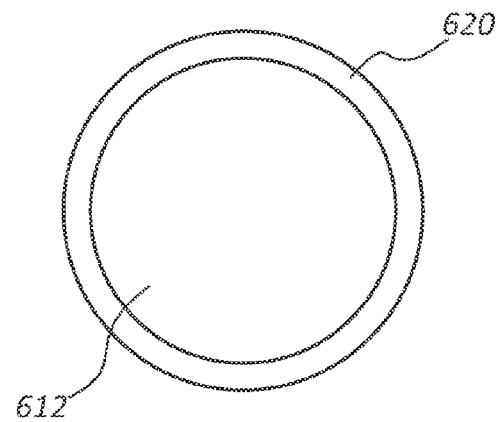
FIG. 6A is a cross sectional view of the balloon catheter of FIG. 5 taken through line 6A-6A.

In one embodiment, balloon 512 comprises a drug-eluting rotational spun coating comprising a therapeutic agent for delivery to a target tissue. For example, as shown in the embodiment depicted in FIG. 6A, showing a cross-section 6A-6A from FIG. 5, the balloon 612 may be coated with a rotational spun coating 620 that includes a therapeutic agent.

Figure 6B:
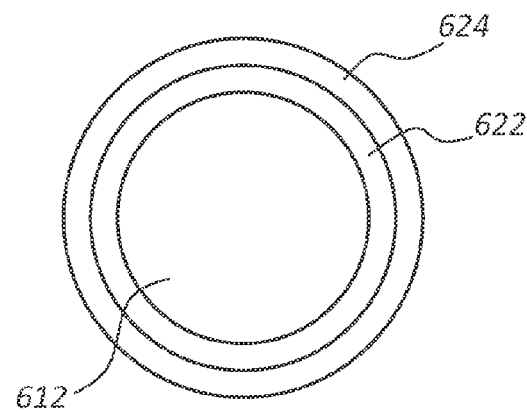
FIG. 6B is another embodiment of a cross sectional view of the balloon catheter of FIG. 5 taken through line 6A-6A.

In some embodiments, the balloon 612 may optionally include an adherent layer. For example, as shown in the embodiment depicted in FIG. 6B, the balloon 612 may be coated with an adherent layer 622 that is covered with a drug-eluting rotational spun coating 624 that includes a therapeutic agent. In such embodiments, the adherent layer 622 may improve the adherence of the drug-eluting rotational spun coating 624 to the surface of the medical device and may help to improve coating integrity. In further embodiments, the adherent layer 622 may improve adherence and/or integrity of a therapeutic agent applied to the rotational spun coating 624. In other embodiments, the adherent layer 622 may function to facilitate a rapid release of the drug-eluting rotational spun layer 624 components from the balloon surface upon contact with tissue at the target site. In other embodiments, the device may further include a top layer. The top layer may reduce loss of the drug-eluting rotational spun coating before it is brought into contact with target tissue, for example during transit of the balloon 612 to the site of therapeutic intervention or during the first moments of inflation of balloon 612 before the drug-eluting rotational spun layer 620 is pressed into direct contact with target tissue.

Figure 6C:
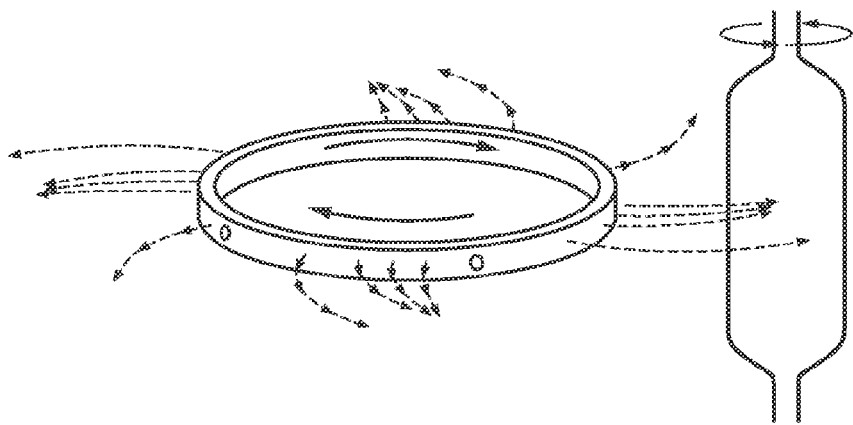
FIG. 6C is a perspective view of an embodiment of a rotational spinning apparatus coating a balloon rotating about its vertical axis.
Figure 6D:
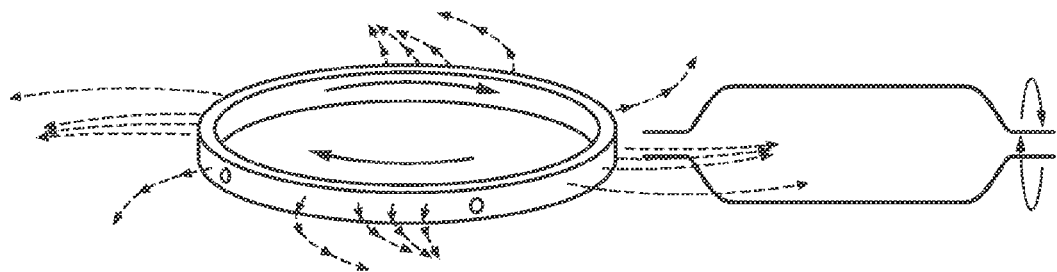
FIG. 6D is a perspective view of an embodiment of a rotational spinning apparatus coating a balloon rotating about its horizontal axis.

In certain embodiments, a medical device comprising a balloon, such as balloon 512 illustrated in FIG. 5, may be coated with drug-eluting rotational spun fiber using, for example, a rotational spinning apparatus 201 as shown in FIGS. 2A and 2B and also shown in FIGS. 6C and 6D. In such embodiments, one or more balloons may be held by the mandrels 216 or used in the place of the mandrels 216 and placed in a generally circular configuration around the spinneret 210. In particular embodiments, shown in FIGS. 6C and 6D, the balloons are inflated while being placed in the rotational spinning fiber field. In some embodiments, the balloons may be stationary, while in other embodiments, the balloons may be configured to rotate about their vertical, horizontal, or a combination of their axes. The thickness and/or density of the rotational spun fibers may be controlled by the orientation of the balloons and/or the duration of time that the balloons are exposed to the spinning fiber field.

The orientation of the rotational spun fiber on the balloon may be controlled by the orientation of the balloon relative to the spinning fiber field and/or by the rotation speed of the balloon during fiber spinning. In such embodiments, multiple layers of rotational spun fibers may be applied to the balloon, wherein one or more layers can have a different orientation from another layer. In particular embodiments, multiple layers of rotational spun fibers may be applied to the balloon, wherein one or more layers comprises a therapeutic agent or a bioabsorbable material that is layered between other layers of the rotational spun fibers. For example, an anti-stenotic drug, such as rapamycin, may be added between the layers to create a controlled release effect. In a further example, a layer of rotational spun fibers comprising a therapeutic agent may be applied to the surface of the balloon to create a rapid release effect. In other embodiments, a layer of rotational spun fibers comprising a therapeutic agent may be coated with a biological or bioabsorbable layer, such as collagen, to provide for the controlled release of the therapeutic agent. In such embodiments, the biological layer itself, such as a collagen layer impregnated with rapamycin, may be applied to the rotational spun fibers using rotational spinning or electrospinning.

In other embodiments, a medical device comprising a balloon as disclosed herein, may comprise a drug-eluting rotational spun coating that is applied by rolling a balloon over a mat of rotational spun fibers. In such embodiments, the orientation of the fibers may be controlled by rolling the balloon over a mat of spun fibers in the desired orientation.

In preparation for coating the balloons with rotational spun fibers, an appropriate material may be placed in the rotational spinning reservoir or spinneret 210. In some embodiments, the material placed in the spinneret 210 is a melt-processable material or a solvent-based material solution. In other embodiments, the material placed in the rotational reservoir comprises a therapeutic agent that has been mixed with the material before the generation of the rotational spun fibers. After a balloon has been coated with a rotational spun coating as described herein, the rotational spun coating may be allowed to cure. In some embodiments, the rotational spun coating may be cured with heat or sintering. In other embodiments, the rotational spun coating may be a self-curing solvent-based material that may be cured by air drying or exposure to heat to dry the solvent. In further embodiments, the rotational spun coating may comprise a melt-processable material and, as such, be cured by cooling. After curing, the coated balloon may be dipped or spray coated with an additional layer of material to reinforce the rotational spun coating and/or to bond the rotational spun coating to the balloon. In further embodiments, a therapeutic agent may be applied to the rotational spun fiber coating on the balloon after the coating has cured.

Also disclosed herein are methods of drug delivery using a medical device comprising a drug-eluting rotational spun coating. The methods of drug delivery disclosed herein comprise the placement of a medical device as disclosed herein near or at a target tissue site, such as a target vessel or lumen of a body. In certain embodiments, the medical device may be positioned, for example using a catheter and/or a guidewire system, or any suitable technique for positioning the device at a location within the body. Once the medical device is positioned at the target location, the medical device may be deployed, thereby placing the drug-eluting rotational spun coating in contact with the target tissue. In some embodiments, the medical device may be a balloon catheter, as disclosed herein, comprising a balloon with a drug-eluting rotational spun coating, wherein the coated balloon is deployed by inflating the balloon at the target tissue site. In other embodiments, the medical device may be a stent, as disclosed herein, comprising a drug-eluting rotational spun coating, wherein the coated stent is deployed by expanding the stent at the target tissue site. When the medical device is deployed, one or more therapeutic agents may be eluted from the rotational spun coating and delivered to the target tissue.

In certain embodiments, the method of delivering a therapeutic agent to a target tissue using a medical device comprising a drug-eluting rotational spun coating, comprises positioning the medical device comprising a drug-eluting rotational spun coating near a target tissue, deploying the medical device, thereby placing the drug-eluting rotational spun coating in contact with the target tissue, and delivering the therapeutic agent to the target tissue by releasing the therapeutic agent from the drug-eluting rotational spun coating in an amount configured to deliver a pharmaceutically effective dose to the target tissue. In some embodiments, the therapeutic agent is associated with the coating via covalent or ionic bonding.

In some embodiments of a method of delivering a drug to a target tissue using a medical device, the therapeutic agent is selected from at least one of rapamycin, paclitaxel, a bismuth-containing compound, heparin, and analogs of any of the foregoing. In certain methods, the drug-eluting rotational spun coating may comprise at least one of nylon 6-6, polyethylene, polypropylene, PTFE, and Kevlar. In other embodiments, the drug-eluting rotational spun coating comprises at least one of the following: fibrin, fibrinogen, chitin, chitosan, starch, collagen, hyaluronic acid, alginate, dextran, cellulose, and mixtures thereof.

In certain embodiments of a method of delivering a drug to a target tissue using a medical device, the drug-eluting rotational spun coating comprises rotational spun fibers approximately one micron in diameter or smaller. In other embodiments, the drug-eluting rotational spun coating comprises rotational spun fibers approximately one micron in diameter or greater.

In particular embodiments of the methods of drug delivery disclosed herein, a medical device comprising a drug-eluting rotational spun coating may be configured to deliver a therapeutic agent in a controlled manner. In certain embodiments, a therapeutic agent may be delivered using a drug-eluting rotational spun coating configured for a delayed, a rapid or an immediate release of the drug. For example, the drug-eluting rotational spun coating may be configured to provide a controlled release of the therapeutic agent to a target tissue. In an embodiment, the coating is configured to provide a controlled release of the therapeutic agent to a target tissue in approximately 5 minutes or less, 4 minutes or less, 3 minutes or less, 2.5 minutes or less, 2 minutes or less, 1.8 minutes or less, 1.6 minutes or less, 1.4 minutes or less, 1.2 minutes or less, 1 minute or less, 0.9 minutes or less, 0.8 minutes or less, 0.7 minutes or less, 0.6 minutes or less, 0.5 minutes or less, 0.4 minutes or less, 0.3 minutes or less, 0.2 minutes or less, or 0.1 minutes or less.

In other embodiments of the methods of drug delivery disclosed herein, a medical device comprising a drug-eluting rotational spun coating may be configured to provide a controlled release of the therapeutic agent over a time period of at least approximately one day, multiple days, a week, multiple weeks, a month, multiple months, a year, or a year or greater. In some embodiments, the therapeutic agent is associated with the drug-eluting rotational spun coating during the rotational spinning of the drug-eluting rotational spun coating. In other embodiments, the therapeutic agent is associated with the drug-eluting rotational spun coating subsequent to the rotational spinning of the drug-eluting rotational spun coating.

In certain embodiments of a method of delivering a drug to a target tissue using a medical device, the drug-eluting rotational spun coating comprises at least two layers of rotational spun fibers. In some embodiments, the drug-eluting rotational spun coating comprises at least one layer of rotational spun fibers and at least one layer of a non-spun material. The drug-eluting rotational spun coating may further comprise an electrospun coating. In further embodiments, the medical devices used for the disclosed methods of delivering a drug to a target tissue are selected from at least one of a balloon, a stent, a catheter or a vascular graft.

Also disclosed herein are methods of manufacturing a medical device comprising a drug-eluting rotational spun coating, the method comprising: rotationally spinning a polymeric material, applying the rotationally spun polymeric material to a substrate of the medical device, and associating a therapeutic agent with the rotationally spun polymeric material. In certain embodiments, the method of manufacturing a medical device has the therapeutic agent associated with the rotational spun coating during rotational spinning of the polymeric material. In some embodiments, the therapeutic agent is associated with the rotational spun coating subsequent to rotational spinning of the polymeric material. In yet further embodiments, the therapeutic agent is mixed with the polymeric material in a dispersion or liquid form prior to rotational spinning of the polymeric material. In an embodiment, the method of manufacturing a medical device further comprises electrospinning a layer of polymeric material that is applied to the substrate of the medical device.

EXAMPLES

A number of exemplary rotational spun structures were produced according to the disclosure herein. FIGS. 7A-21 are scanning electron micrographs (SEMs) of the rotational spun structures produced in an exemplary process. The following examples (some of which are prophetic) are intended to further illustrate exemplary embodiments and are not intended to limit the scope of the disclosure.

Example 1

A drug-eluting rotational spun coating is applied to a balloon according to the current disclosure. Polyamide 6 (nylon 6) is dissolved in 1,1,1,3,3,3-hexafluoro-2-propanol to create three solutions, one comprising 9% nylon 6 by weight, one comprising 13% nylon 6 by weight, and one comprising 15% nylon 6 by weight. To each solution is added approximately 50-150 mg of rapamycin. Each solution is then rotationally spun from a spinneret rotating between about 7500 RPM and about 8000 RPM. The spinneret is configured with 26 gauge needle orifices.

The second solution, comprising 13% nylon 6 by weight, is rotationally spun at 7500 RPM onto a horizontally mounted balloon (similar to arrangement shown in FIG. 6C) rotating at about 200 RPM.

Example 2

Polyamide 6 (nylon 6) was dissolved in 1,1,1,3,3,3-hexafluoro-2-propanol to create three solutions, one comprising 9% nylon 6 by weight, one comprising 13% nylon 6 by weight, and one comprising 15% nylon 6 by weight. Each solution was then rotationally spun from a spinneret rotating between about 7500 RPM and about 8000 RPM. The spinneret was configured with 26 gauge needle orifices.

Generally, it was observed that the higher weight percent nylon 6 solutions spun better at higher rotational speeds as the solution was more viscous. Each solution produced relatively well-defined fibers. It was observed that the higher concentration solutions produced stronger fibers. Finally, it was observed that, while rotationally spinning the solution, the solvent tended to evaporate relatively quickly.

The second solution, comprising 13% nylon 6 by weight, was rotationally spun at 7,500 RPM onto a horizontally mounted inflated balloon (similar to the arrangement of FIG. 6D) rotating at about 200 RPM. This created a uniform microfiber rotational spun coating on the balloon.

Additionally, the nylon fibers were rotationally spun onto an un-inflated balloon, or parison, which was later inflated to the desired shape. During inflation, the rotationally spun fibers remained intact and stretched as the balloon was expanded. After inflation, the rotationally spun nylon fiber coating did not show any signs of breakage, showing that the fiber coatings may be deposited on a balloon prior to inflation of the balloon.

Figure 17:
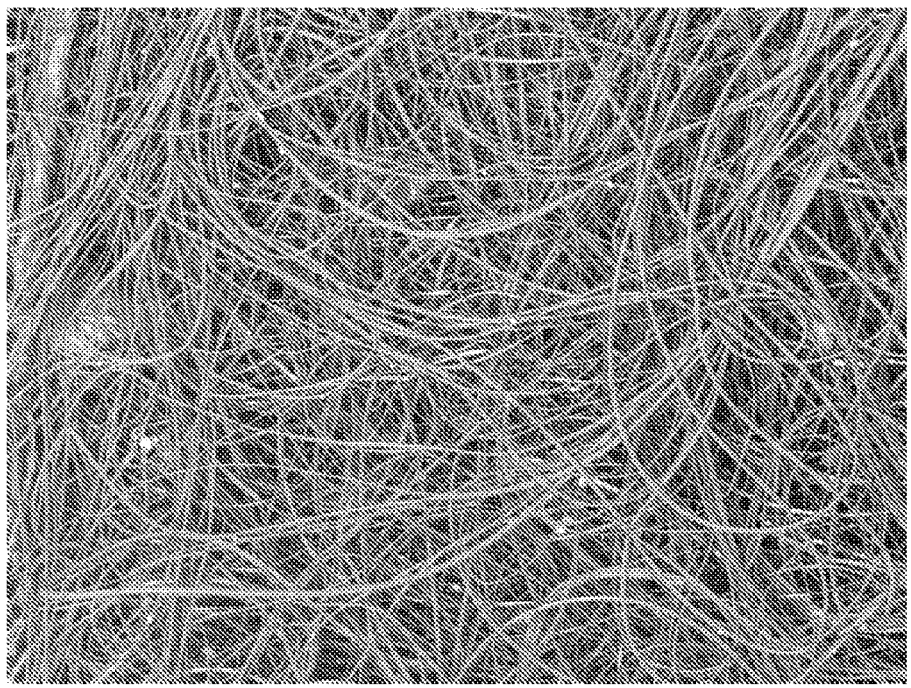
FIG. 17 is a SEM of a rotational spun nylon coating at 170× magnification.
Figure 18:
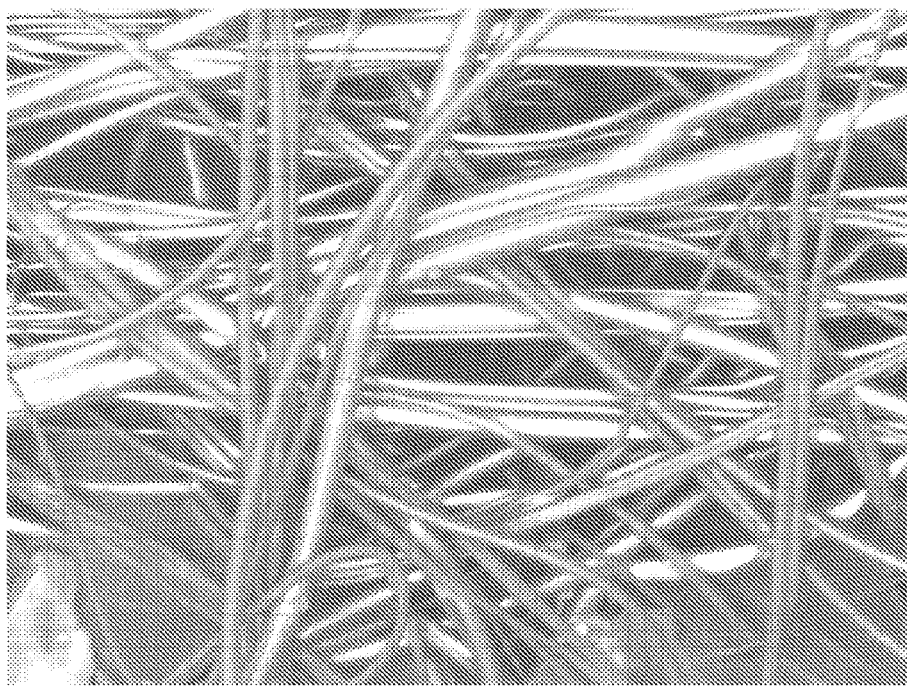
FIG. 18 is an SEM of the nylon coating of FIG. 17 at 950× magnification.

FIG. 17 is a scanning electron micrograph (SEM) of a nylon coating at 170× magnification. FIG. 18 is an SEM of the nylon coating at 950× magnification.

Example 3

A drug-eluting rotational spun coating is applied to a stent according to the current disclosure. A 60 wt % PTFE water dispersion is mixed with PEO and water as follows: Water is added to PEO to maintain a ratio of 2.86 ml of water per gram of PEO. The water and PEO are mixed until the PEO is fully dissolved and the solution creates a thick gel. 24.00 ml of 60 wt % PTFE aqueous dispersion is added to the dissolved PEO to obtain a 0.07 g/ml mixture of PEO to PTFE dispersion. The mixture is strained through a 70 micrometer or finer filter to remove any large particles. The combined solution is then allowed to sit and/or is mixed in a non-agitating jar roller until the solution achieves homogeneity; in some instances that process takes 24 to 48 hours.

The solution is then rotationally spun from a spinneret at about 3500 RPM and collected on a rotating stent. The stent is rotated at about 200 RPM during this example. The stent is positioned between about 4 inches and about 6 inches away from the spinneret, along the length of the balloon. The orifices on the spinneret are about 30 gauge openings. The rotational spun coating on the stent is then sintered at about 385° C. for about 10 minutes. At least one therapeutic agent, such as rapamycin, paclitaxel, and/or heparin, is then applied to the rotational spun coating after sintering by spraying, brushing, rolling, dipping, or other appropriate methods. In this example, a solution of rapamycin is prepared by dissolving rapamycin in ethanol. The rapamycin/ethanol solution is sprayed onto the rotational spun coating and the solution is allowed to penetrate the porous structure of the PTFE rotational spun coating. After applying the solution, the ethanol evaporates leaving the rapamycin distributed in the drug-eluting rotational spun coating. In a further example, heparin is applied to the rotational spun coating by dipping, spraying, or brushing. In one such example, heparin is applied to the rotational spun coating such that the heparin is covalently bonded to the rotational spun coating fibers.

To at least a portion of the drug-eluting rotational spun coating is applied an additional layer of rotational spun, electrospun, sprayed, or dipped biological or synthetic material to immobilize the therapeutic agent and/or to control the release rate of the therapeutic agent.

Example 4

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 25.71 ml of 60 wt % PTFE aqueous dispersion was added to the dissolved PEO to obtain a 0.05 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotationally spun from a spinneret at about 3000 RPM and collected on a 2 inch by 2 inch sheet of aluminum foil. The collection sheet was positioned about 10 inches from the spinneret. The orifices on the spinneret were about 30 gauge openings. The mat was then sintered at about 385° C. for about 10 minutes.

Small beads were observed on the fibers produced in this example. The resultant mat was about 50 micrometers thick. It was further observed that the mat was generally very open. Similarly, the fiber diameters observed were generally small to medium in diameter (i.e. less than about 750 nanometers in diameter to about 2 microns in diameter).

Figure 7A:
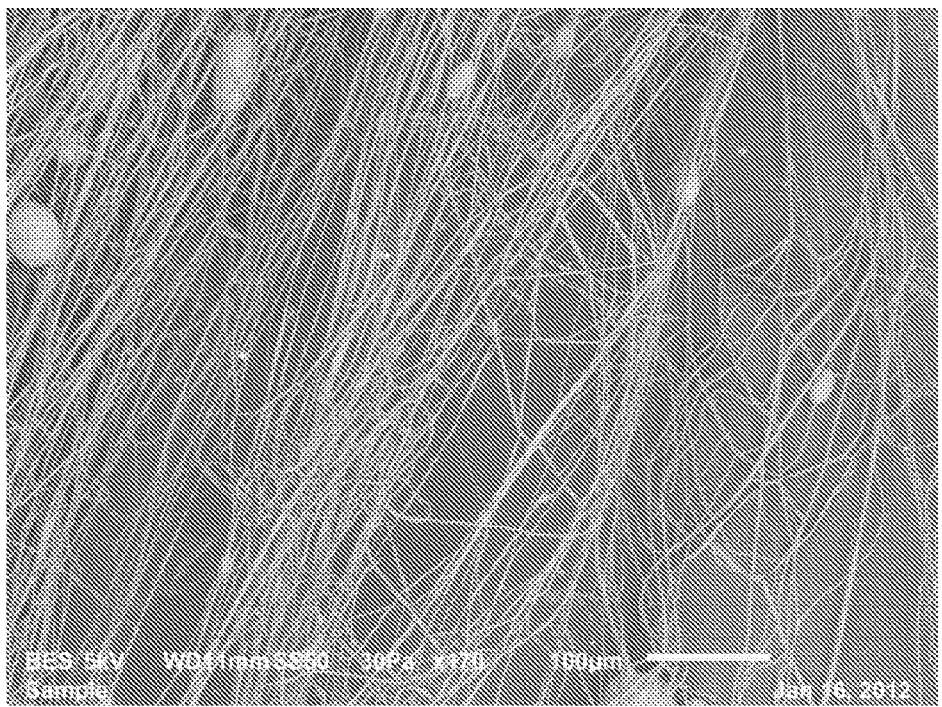
FIG. 7A is a scanning electron micrograph (SEM) of a rotational spun material created from a polytetrafluoroethylene (PTFE) dispersion combined with polyethylene oxide (PEO) and water.
Figure 7B:
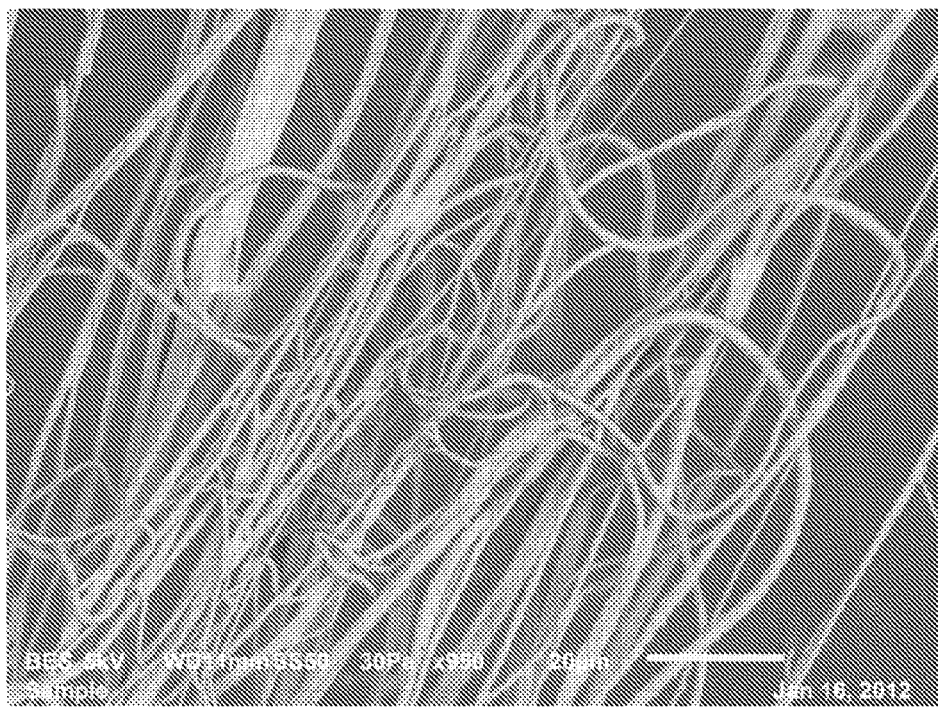
FIG. 7B is an SEM of the material of FIG. 7A at a greater level of magnification.

FIG. 7A is an SEM of the rotational spun PTFE mat created in the procedure of Example 4. FIG. 7A reflects a magnification of 170×. FIG. 7B is an SEM of the rotational spun PTFE of FIG. 7A at a magnification of 950×.

A therapeutic agent may be used with the rotational spun PTFE mat of Example 4. For example, approximately 20-500 mg of rapamycin or paclitaxel may be added to the PTFE dispersion before rotational spinning. Alternatively, rapamycin or paclitaxel may be applied directly by spraying or dipping the mat after sintering. Furthermore, rapamycin or paclitaxel may be combined with a biological material, such as collagen, and applied as a rotational spun or electrospun layer to the mat.

Example 5

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 24.00 ml of 60 wt % PTFE aqueous dispersion was added to the dissolved PEO to obtain a 0.07 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotationally spun from a spinneret at about 4500 RPM and collected on a 2 inch by 2 inch sheet of aluminum foil. The collection sheet was positioned about 9.5 inches from the spinneret. The orifices on the spinneret were about 30 gauge openings. The mat was then sintered at about 385° C. for about 10 minutes.

The generally random deposition of the fibers as well as the intersecting or crossing nature of fibers may be seen in this example. The resultant mat was about 50 micrometers thick. It was further observed that the mat was generally open. Similarly, the fiber diameters observed were generally of medium diameter, i.e. between about 750 nanometers and about 2 microns in diameter.

Figure 8A:
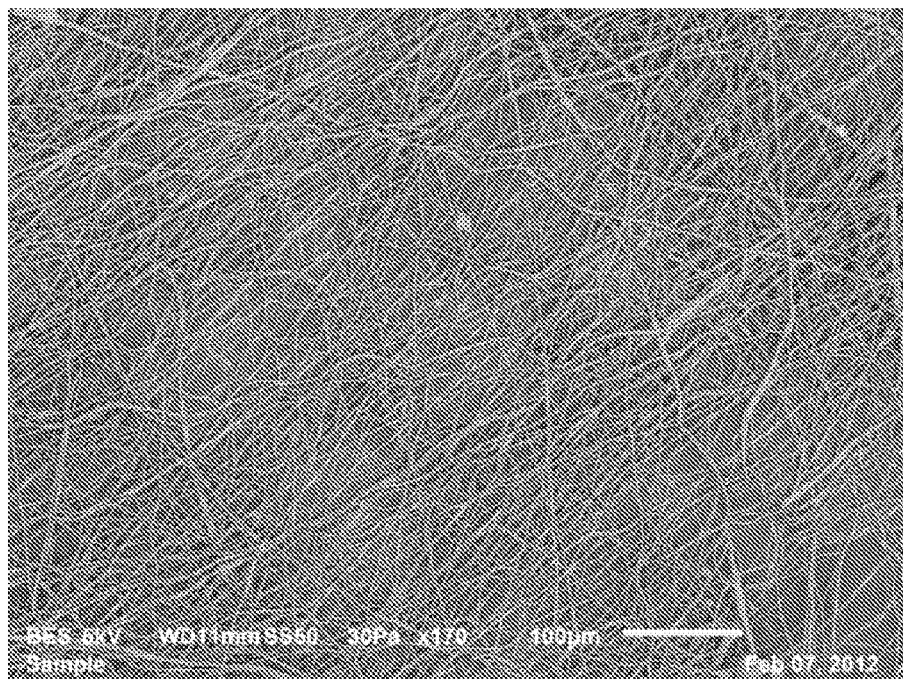
FIG. 8A is an SEM of a rotational spun material having medium fiber diameters which were collected on a sheet.
Figure 8B:
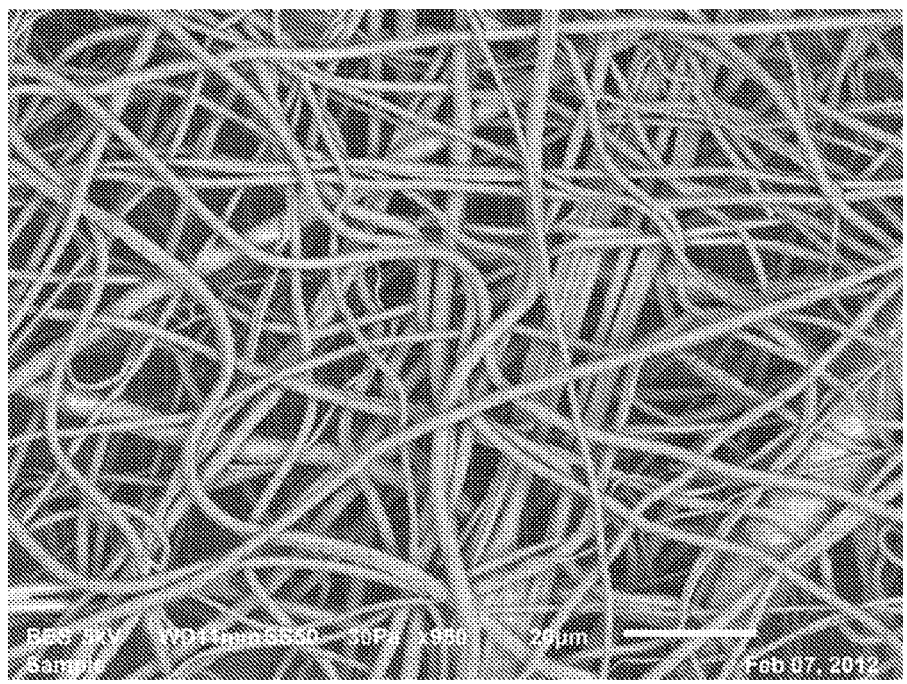
FIG. 8B is an SEM of the material of FIG. 8A at a greater level of magnification.

FIG. 8A is an SEM of the rotational spun PTFE mat created in the procedure of Example 5. FIG. 8A reflects a magnification of 170×. FIG. 8B is an SEM of the rotational spun PTFE of FIG. 8A at a magnification of 950×.

A therapeutic agent may be used with the rotational spun PTFE mat of Example 5. For example, approximately 20-500 mg of rapamycin or paclitaxel may be added to the PTFE dispersion before rotational spinning or applied to the mat after curing.

Example 6

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 24.00 ml of 60 wt % PTFE aqueous dispersion was added to the dissolved PEO to obtain a 0.07 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotationally spun from a spinneret at about 4500 RPM and collected on a 0.5 inch diameter rotating mandrel. The mandrel was rotated at about 200 RPM during this example. The mandrel was positioned about 9.5 inches from the spinneret. The orifices on the spinneret were about 30 gauge openings. The mat was then sintered at about 385° C. for about 10 minutes.

It was observed that the fibers of the mat obtained in this example were generally aligned. The resultant mat was about 50 micrometers thick. It was further observed that the mat was generally less open. Similarly, the fiber diameters observed were generally of medium diameter, i.e. between about 750 nanometers and about 2 microns in diameter.

Figure 9A:
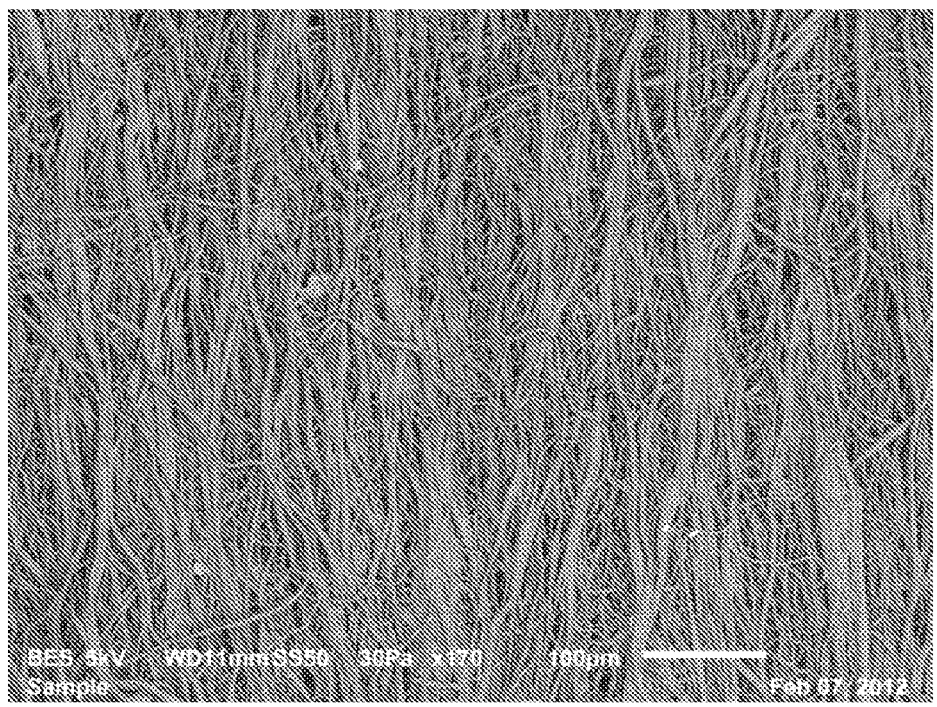
FIG. 9A is an SEM of a rotational spun material having medium fiber diameters which were collected on a rotating mandrel.
Figure 9B:
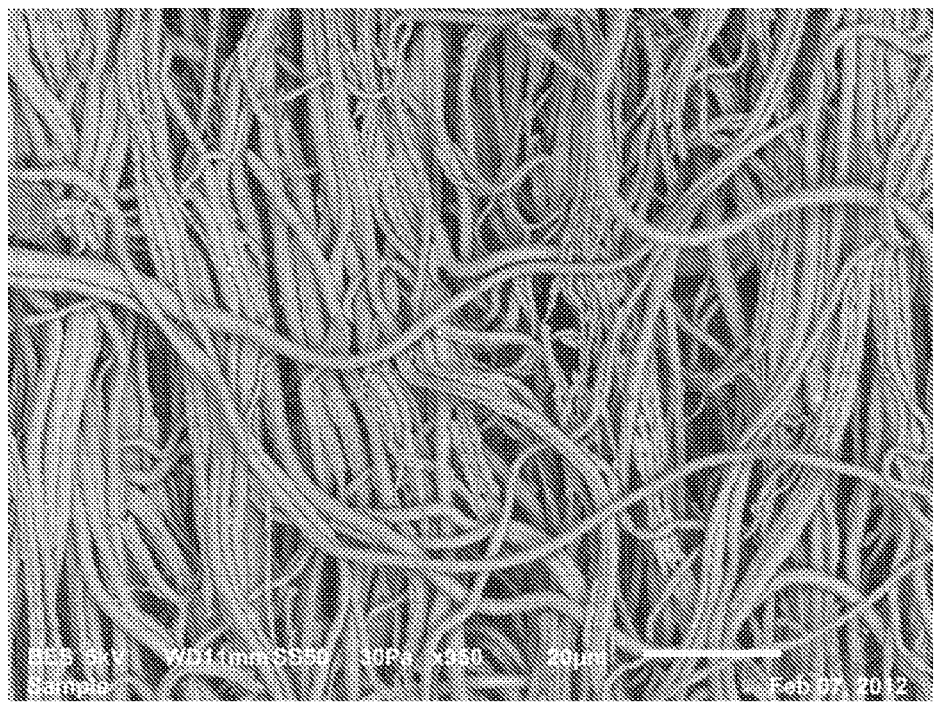
FIG. 9B is an SEM of the material of FIG. 9A at a greater level of magnification.

FIG. 9A is an SEM of the rotational spun PTFE mat created in the procedure of Example 6. FIG. 9A reflects a magnification of 170×. FIG. 9A illustrates the generally more aligned dispositions of fibers collected on a rotating mandrel. In particular, comparison of FIGS. 8A and 9A illustrates the effect of the use of a rotating mandrel as opposed to a sheet collector, with respect to fiber alignment. FIG. 9B is an SEM of the rotational spun PTFE of FIG. 9A at a magnification of 950×.

A therapeutic agent may be used with the rotational spun PTFE mat of Example 6. For example, approximately 20-500 mg of rapamycin or paclitaxel may be added to the PTFE dispersion before rotational spinning or applied to the mat after curing.

Example 7

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 21.43 ml of 60 wt % PTFE aqueous dispersion was added to the dissolved PEO to obtain a 0.10 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotationally spun from a spinneret at about 6000 RPM and collected on a 0.5 inch diameter rotating mandrel. The mandrel was rotated at about 200 RPM during this example. The mandrel was positioned about 9.5 inches from the spinneret. The orifices on the spinneret were about 30 gauge openings. The mat was then sintered at about 385° C. for about 10 minutes.

It was observed that the fibers of the mat obtained in this example were generally aligned. The resultant mat was about 50 micrometers thick. It was further observed that the mat was generally open. Similarly, the fiber diameters observed were generally of large diameter, i.e. at least about 2 microns and up to about 1 millimeter in diameter.

Figure 10A:
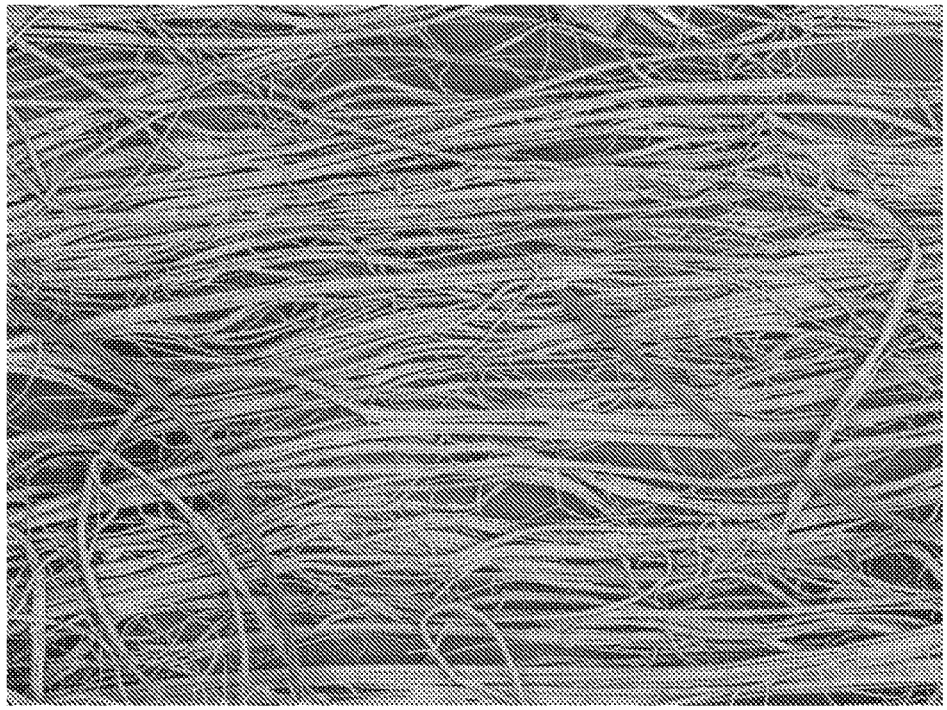
FIG. 10A is an SEM of a rotational spun material having larger fibers which were collected on a rotating mandrel, at a magnification of 170×.
Figure 10B:
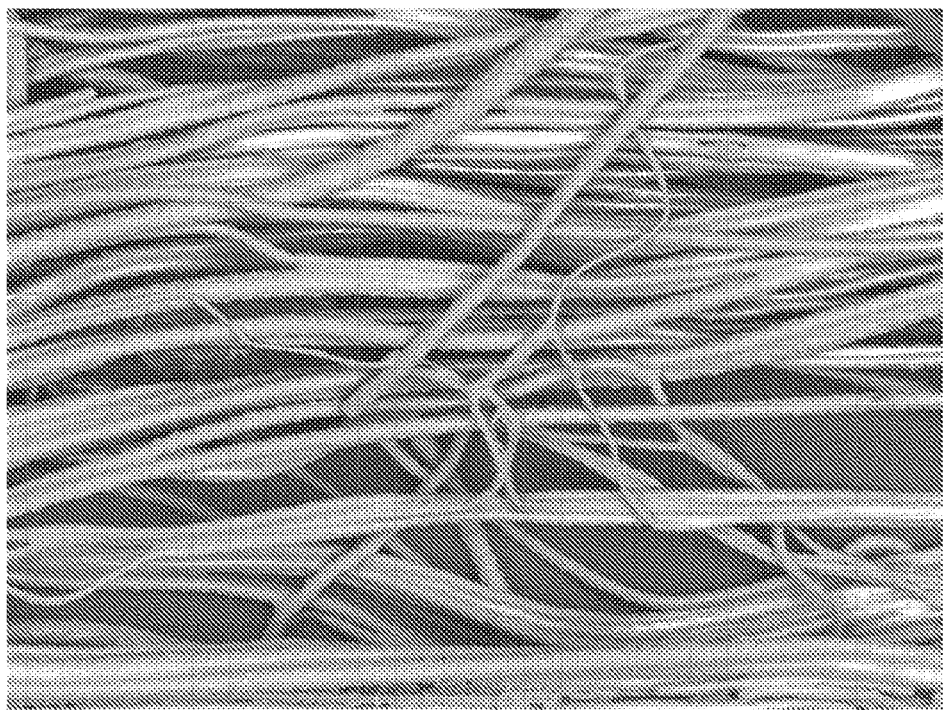
FIG. 10B is an SEM of the material of FIG. 10A at a magnification of 950×.

FIG. 10A is an SEM of the rotational spun PTFE mat created in the procedure of Example 7. FIG. 10A reflects a magnification of 170×. FIG. 10B is an SEM of the rotational spun PTFE of FIG. 10A at a magnification of 950×.

A therapeutic agent may be used with the rotational spun PTFE mat of Example 7. For example, approximately 20-500 mg of rapamycin or paclitaxel may be added to the PTFE dispersion before rotational spinning or applied to the mat after curing.

Example 8

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 20.56 ml of 60 wt % PTFE aqueous dispersion was added to the dissolved PEO to obtain a 0.11 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotationally spun from a spinneret at about 8000 RPM and collected on a 2 inch by 2 inch sheet of aluminum foil. The collection sheet was positioned about 9.5 inches from the spinneret. The orifices on the spinneret were about 30 gauge openings. The mat was then sintered at about 385° C. for about 10 minutes.

It was observed that the mat created in this example had a large distribution of fiber diameters, including some large fibers. The resultant mat was about 50 micrometers thick. It was further observed that the mat was generally open. Similarly, the fiber diameters observed were generally of large diameter, i.e. at least about 2 microns and up to about 1 millimeter in diameter.

Figure 11:
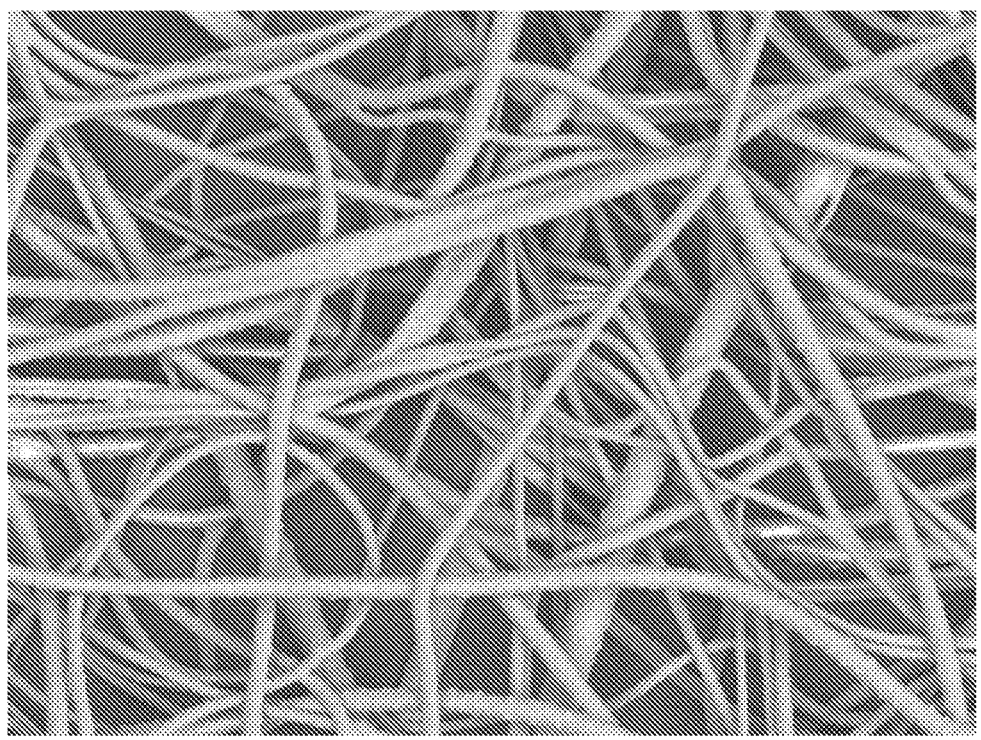
FIG. 11 is an SEM of a rotational spun material having larger fibers which were collected on a sheet, at a magnification of 950×.

FIG. 11 is an SEM of the rotational spun PTFE mat created in the procedure of Example 8. FIG. 11 reflects a magnification of 950×.

A therapeutic agent may be used with the rotational spun PTFE mat of Example 8. For example, approximately 20-500 mg of rapamycin or paclitaxel may be added to the PTFE dispersion before rotational spinning or applied to the mat after curing.

Example 9

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 21.43 ml of 60 wt % PTFE aqueous dispersion was added to the dissolved PEO to obtain a 0.10 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotationally spun from a spinneret at about 6000 RPM and collected on a 2 inch by 2 inch sheet of aluminum foil. The collection sheet was positioned about 9.5 inches from the spinneret. The orifices on the spinneret were about 30 gauge openings. The mat was then sintered at about 385° C. for about 10 minutes.

No beading was observed on the fibers of this mat. The resultant mat was about 50 micrometers thick. It was further observed that the mat was generally less open. Similarly, the fiber diameters observed were generally of medium diameter, i.e. between about 750 nanometers and about 2 microns in diameter.

Figure 12A:
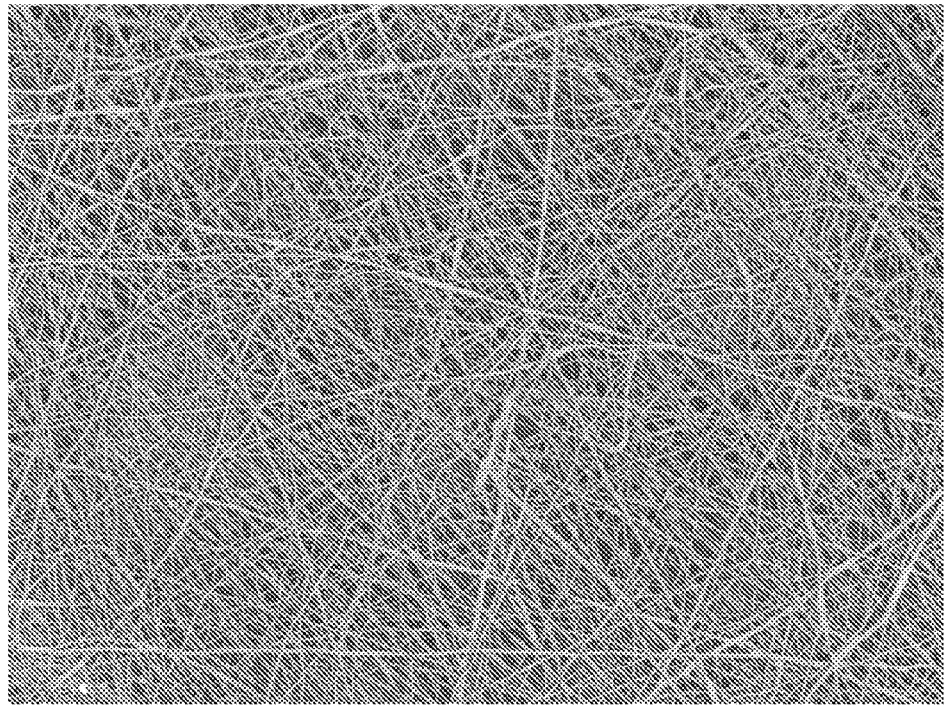
FIG. 12A is an SEM of a rotational spun material having medium fibers which were collected on a sheet, at a magnification of 170×.
Figure 12B:
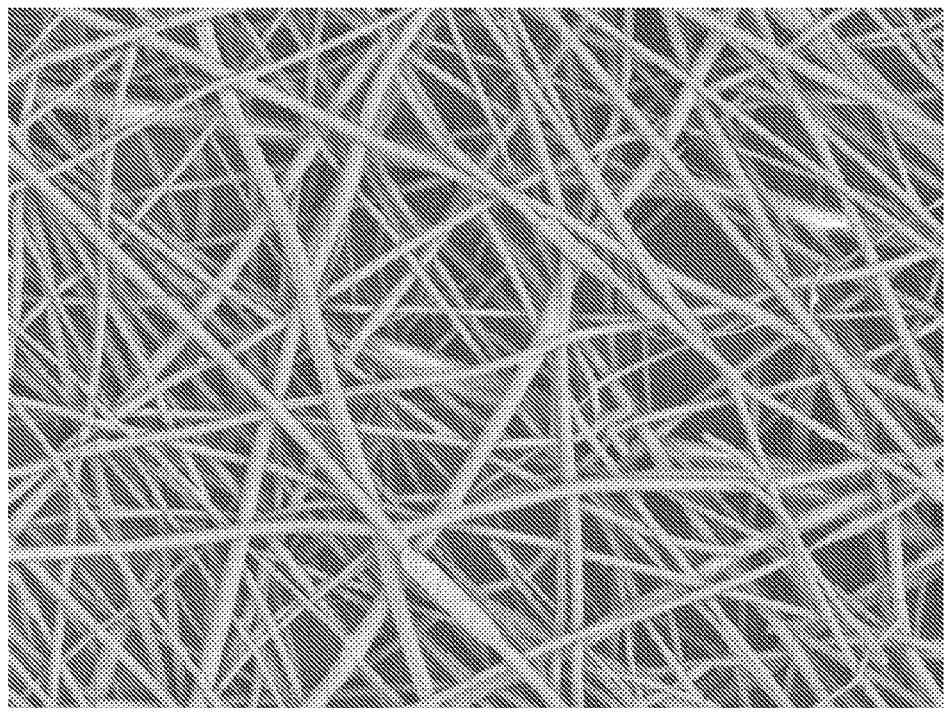
FIG. 12B is an SEM of the material of FIG. 12A at a magnification of 950×.

FIG. 12A is an SEM of the rotational spun PTFE mat created in the procedure of Example 9. FIG. 12A reflects a magnification of 170×. FIG. 12B is an SEM of the rotational spun PTFE of FIG. 12A at a magnification of 950×.

A therapeutic agent may be used with the rotational spun PTFE mat of Example 9. For example, approximately 20-500 mg of rapamycin or paclitaxel may be added to the PTFE dispersion before rotational spinning or applied to the mat after curing.

Example 10

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 25.71 ml of 60 wt % PTFE aqueous dispersion was added to the dissolved PEO to obtain a 0.05 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotationally spun from a spinneret at about 3000 RPM and collected on a 2 inch by 2 inch sheet of aluminum foil. The collection sheet was positioned about 10 inches from the spinneret. The orifices on the spinneret were about 30 gauge openings. The mat was then sintered at about 385° C. for about 10 minutes.

This example produced the smallest diameter fibers of the examples herein disclosed. The resultant mat was about 50 micrometers thick. It was further observed that the mat was generally closed. Again, the fiber diameters observed were generally of small diameter, i.e. less than about 750 nanometers in diameter.

Figure 13A:
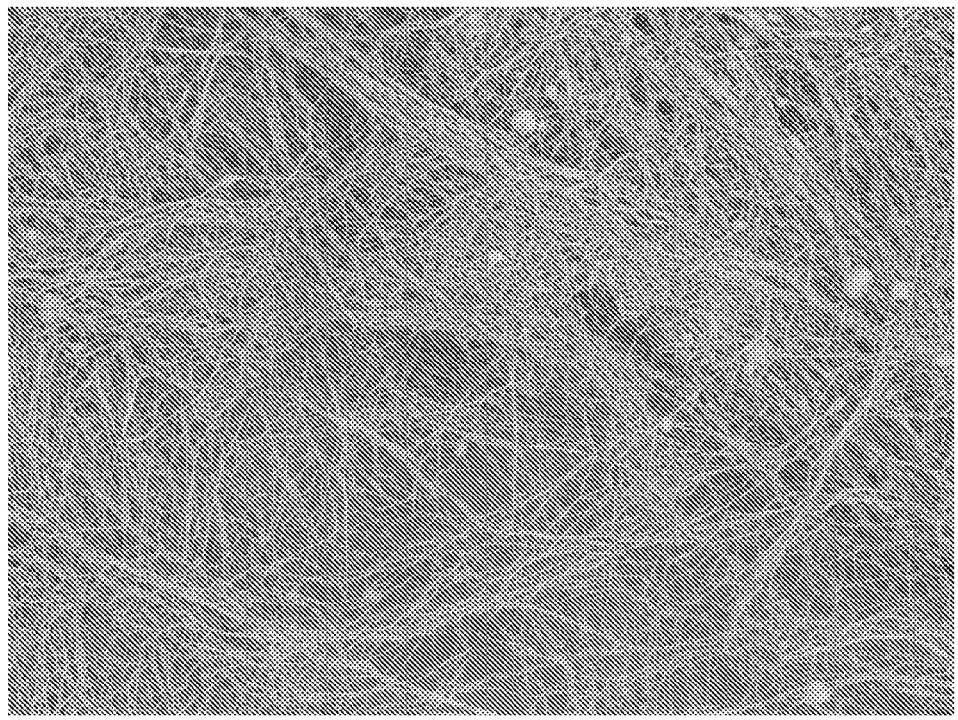
FIG. 13A is an SEM of a rotational spun material having smaller fibers which were collected on a sheet, at a magnification of 170×.
Figure 13B:
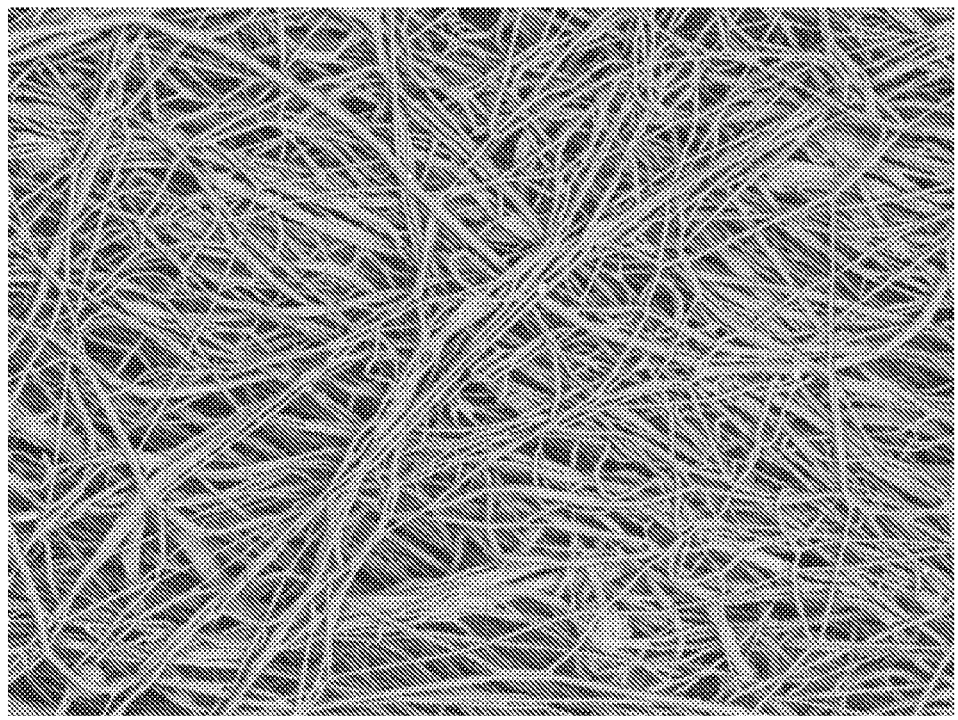
FIG. 13B is an SEM of the material of FIG. 13A at a magnification of 950×.

FIG. 13A is an SEM of the rotational spun PTFE mat created in the procedure of Example 10. FIG. 13A reflects a magnification of 170×. FIG. 13B is an SEM of the rotational spun PTFE of FIG. 13A at a magnification of 950×.

A therapeutic agent may be used with the rotational spun PTFE mat of Example 10. For example, approximately 20-500 mg of rapamycin or paclitaxel may be added to the PTFE dispersion before rotational spinning or applied to the mat after curing.

Example 11

A 60 wt % PTFE water dispersion was mixed with PEO and water as follows. Water was added to PEO to maintain a ratio of 2.86 ml of water per gram of PEO. The water and PEO were mixed until the PEO was fully dissolved and the solution created a thick gel. 24.00 ml of 60 wt % PTFE aqueous dispersion was added to the dissolved PEO to obtain a 0.07 g/ml mixture of PEO to PTFE dispersion. The mixture was strained through a 70 micrometer or finer filter to remove any large particles. The combined solution was then allowed to sit and/or mixed in a non-agitating jar roller until the solution achieved homogeneity; in some instances that process takes 24 to 48 hours.

The combined solution was then rotationally spun from a spinneret at about 3500 RPM and collected on a 0.5 inch diameter rotating mandrel. The mandrel was rotated at about 200 RPM during this example. The mandrel was positioned horizontally in this example. The mandrel was positioned between about 4 inches and about 6 inches away from the spinneret, along the length of the mandrel. The orifices on the spinneret were about 30 gauge openings. The mat was then sintered at about 385° C. for about 10 minutes.

The resultant mat was about 45 micrometers thick. It was further observed that the mat was generally closed. Similarly, the fiber diameters observed were generally of medium diameter, i.e. between about 750 nanometers and about 2 microns in diameter.

Figure 14A:
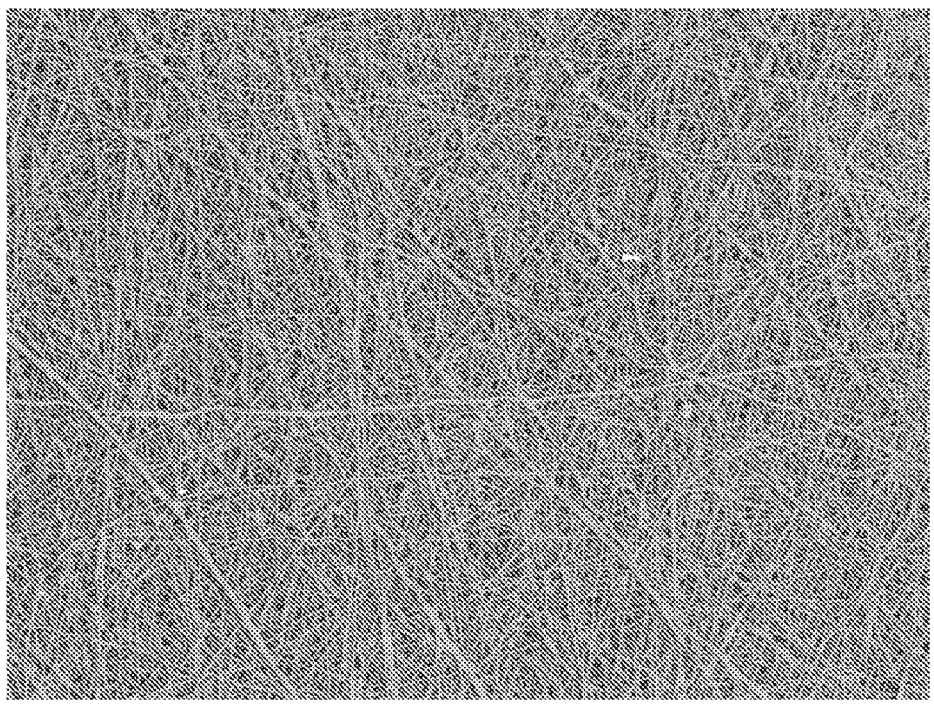
FIG. 14A is an SEM of a rotational spun material collected on a horizontally mounted mandrel, at a magnification of 170×.
Figure 14B:
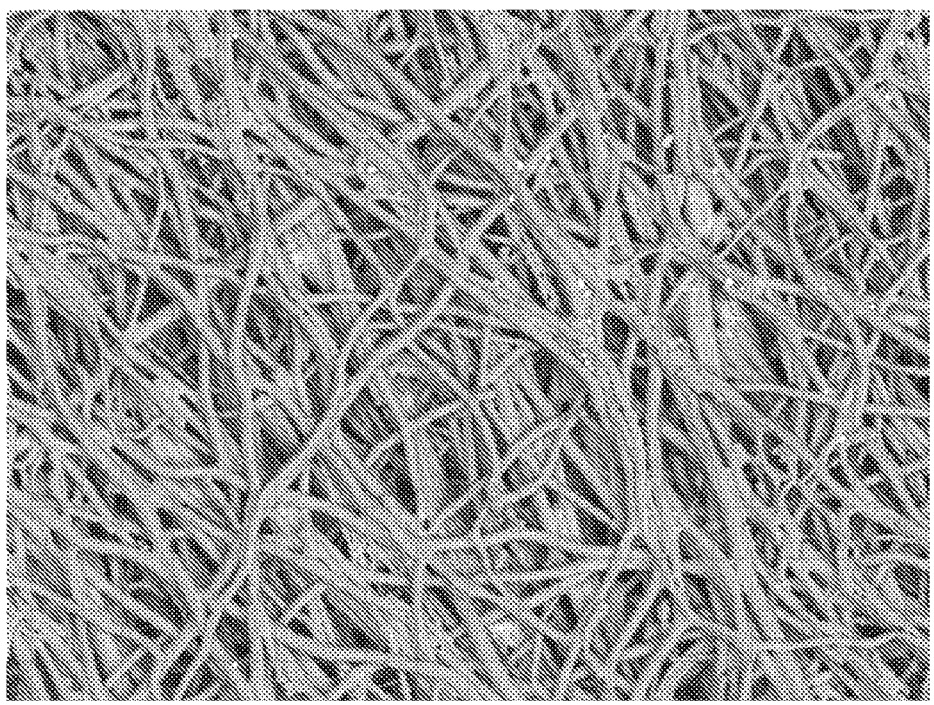
FIG. 14B is an SEM of the material of FIG. 14A at a magnification of 950×.

FIG. 14A is an SEM of the rotational spun PTFE mat created in the procedure of Example 11, at a magnification of 170×. FIG. 14B is an SEM of the rotational spun PTFE of FIG. 14A at a magnification of 950×.

A therapeutic agent may be used with the rotational spun PTFE mat of Example 11. For example, approximately 20-500 mg of rapamycin or paclitaxel may be added to the PTFE dispersion before rotational spinning or applied to the mat after curing.

Example 12

Two separate nanofiber tubes were produced on a horizontal rotating mandrel and each tube removed from the mandrel.

Each tube was produced according to the procedure recited in Example 11. The first of the two tubes was then placed on a 0.5 inch diameter mandrel and a solid 0.001 inch thick FEP (fluorinated ethylene propylene) film was wrapped one time around the first tube and mandrel. The FEP film was tacked in place with a soldering iron at about 320° C.

The second nanofiber tube was then pulled over the FEP film layer and the entire construct placed in an oven for about 21 minutes at about 330° C. The construct was removed from the oven and allowed to cool, and the construct removed from the mandrel.

Figure 15:
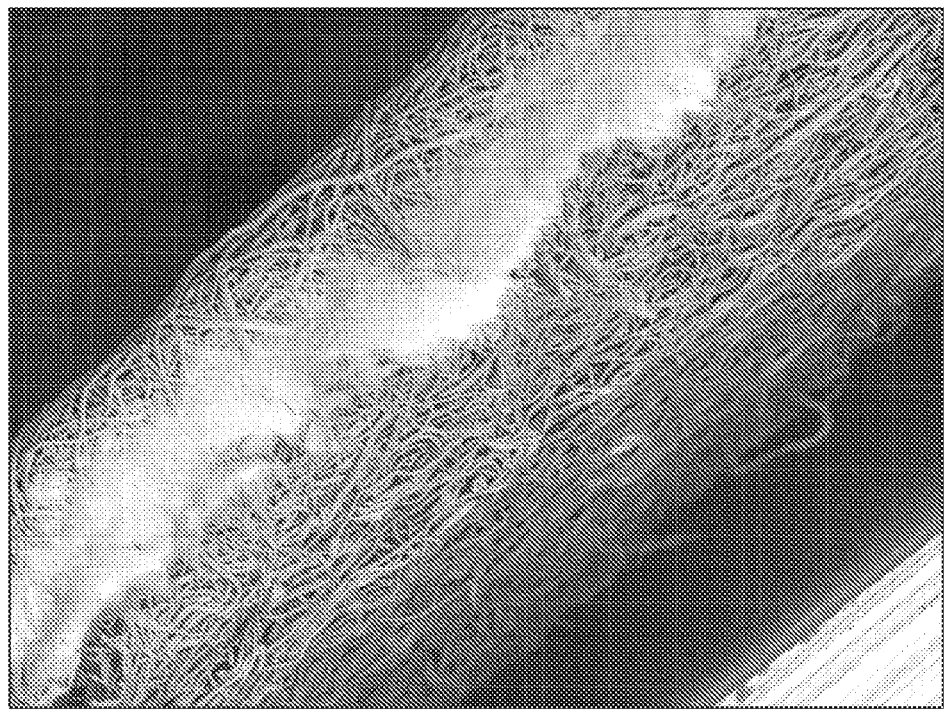
FIG. 15 is an SEM of a cross sectional view of an exemplary construct of multiple layers of rotational spun materials, at a magnification of 370×.

FIG. 15 is an SEM of a cross sectional view of this layered construct at a magnification of 370×. As shown in this figure, the top and bottom layers comprise nanofiber mats, while the middle FEP layer may be configured to be more impervious to tissue ingrowth and/or attachment.

Example 13

A 0.07 g/ml mixture of PEO to PTFE dispersion was rotationally spun from a spinneret at about 3500 RPM and collected on a rotating mandrel. The mandrel was rotated at about 200 RPM and was positioned horizontally in this example. The mandrel was positioned between about 4 inches and about 6 inches away from the spinneret, along the length of the mandrel. The orifices on the spinneret were about 30 gauge openings. The mat was then sintered at about 385° C. for about 10 minutes.

An FEP film was then placed around the mat and mandrel and an overwrap material applied to compress the construct. The construct was then heated to about 330° C. for about 21 minutes. The FEP partially melted and flowed into the gaps or open spaces in the initially formed mat. The compression wrap was then removed.

Figure 16:
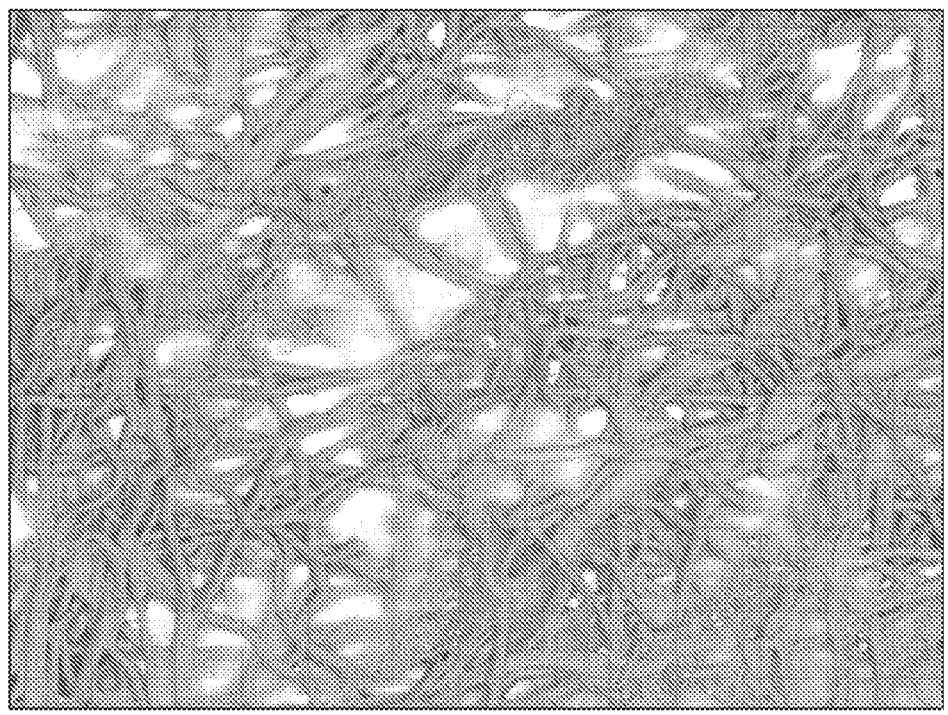
FIG. 16 is an SEM of a construct comprising a rotational spun PTFE material and an FEP (fluorinated ethylene propylene) layer at a magnification of 950×.

FIG. 16 is an SEM of the PTFE/FEP construct at a magnification of 950×. The disposition and interaction of the FEP with respect to the PTFE can be seen.

A therapeutic agent may be used with the rotational spun PTFE/PEO mat of Example 13. For example, approximately 20-500 mg of rapamycin or paclitaxel may be added to the PTFE/PEO dispersion before rotational spinning or applied to the mat after curing.

Example 14

A multilayer rotational spun coating comprising bismuth was prepared containing an FEP-loaded bismuth midlayer (Bi/FEP Stripe) sandwiched between rotationally spun PTFE layers.

For the PTFE rotational spun layers, a 0.07 g/ml mixture of PEO to PTFE dispersion was rotationally spun from a spinneret at about 3,500 RPM and collected on a rotating mandrel. The mandrel was rotated at about 200 RPM in a horizontal position between about 4 inches and about 6 inches away from the spinneret, along the length of the mandrel. The orifices on the spinneret were about 30 gauge openings. The mat was then sintered at about 385° C. for about 10 minutes. The PTFE mat was then dipped in a 5:2 ratio mixture of FEP and water and dried and sintered at 325° C. for about 15 minutes.

For the bismuth midlayer, approximately 0.5 grams bismuth powder (Sigma Aldrich 265462, 100 mesh, 99% purity) was mixed with 2 mL FEP 55% aqueous dispersion (DuPont TE9568) in a 3 mL syringe. The FEP dipped mat was coated with the bismuth/FEP mixture by ejecting the syringe contents over the mat. The bismuth/FEP coated mat was then coated with a second layer of the PTFE rotational spun material and sintered at 385° C. for about 15 minutes. The resulting structure comprising the Bi/FEP Stripe sandwiched between rotationally spun PTFE layers had a thickness of approximately 57 µm, a porosity of approximately 47.96%, and an average fiber diameter of approximately 1.48 µm.

Figure 19:
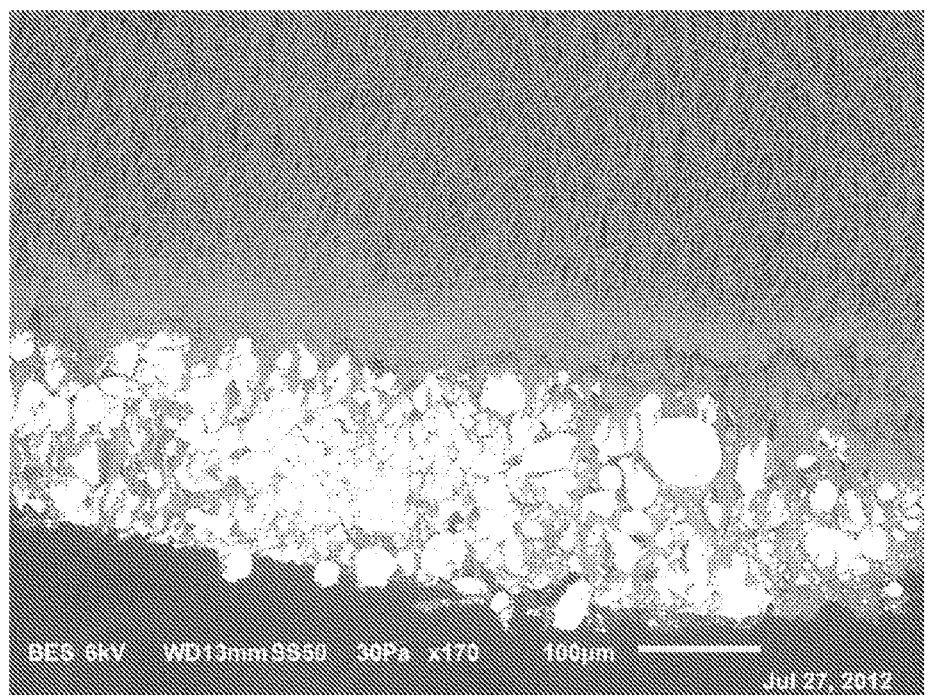
FIG. 19 is an SEM of a rotational spun coating including a bismuth midlayer.

FIG. 19 is an SEM of the PTFE/PEO mat with the Bi/FEP Stripe midlayer at a magnification of 170×.

Example 15

A rotational spun coating was prepared using bismuth subcarbonate combined with a PTFE/PEO mixture. A 60 wt % dispersion of bismuth subcarbonate (Tyco 0288, bismuth subcarbonate blend ZS, with zinc stearate; $(BiO)_2CO_3$) was prepared in water by mixing approximately 12 g bismuth subcarbonate into 20 mL of water. Approximately 3.5 g of PEO and 4.39 mL DI water was mixed with the bismuth subcarbonate dispersion to produce a 0.144 g/mL PEO/bismuth subcarbonate mixture. Next were added 20 mL of PTFE to the PEO/bismuth subcarbonate mixture.

The PTFE/PEO/bismuth subcarbonate mixture was rotationally spun at approximately 2,000-3,000 RPM through a 25 gauge size opening for approximately 1 minute to create a rotationally spun fiber mat.

Figure 20:
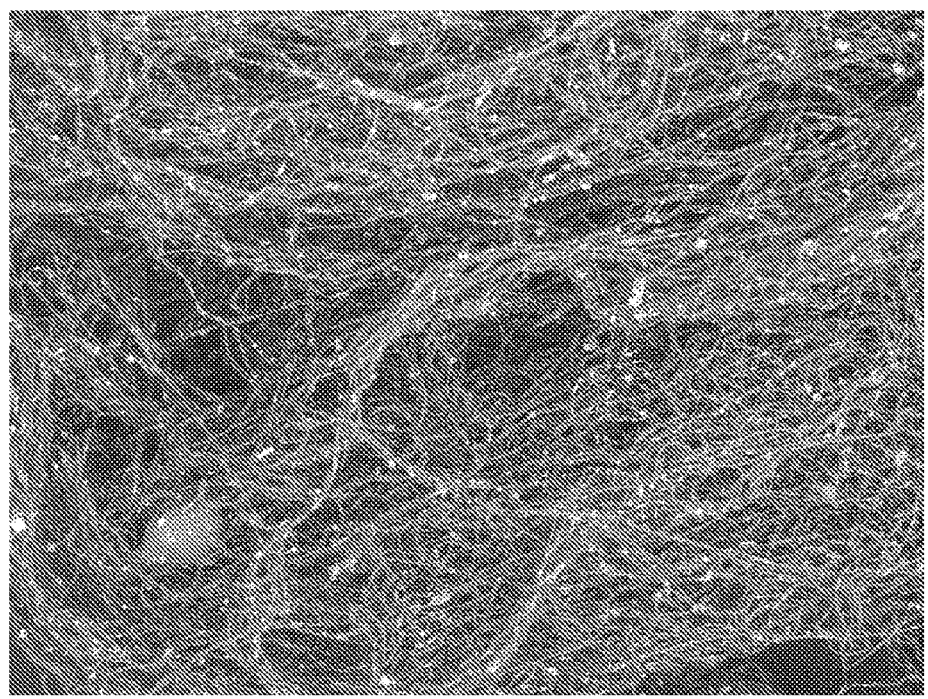
FIG. 20 is an SEM of a rotational spun coating including bismuth subcarbonate at 170× magnification.
Figure 21:
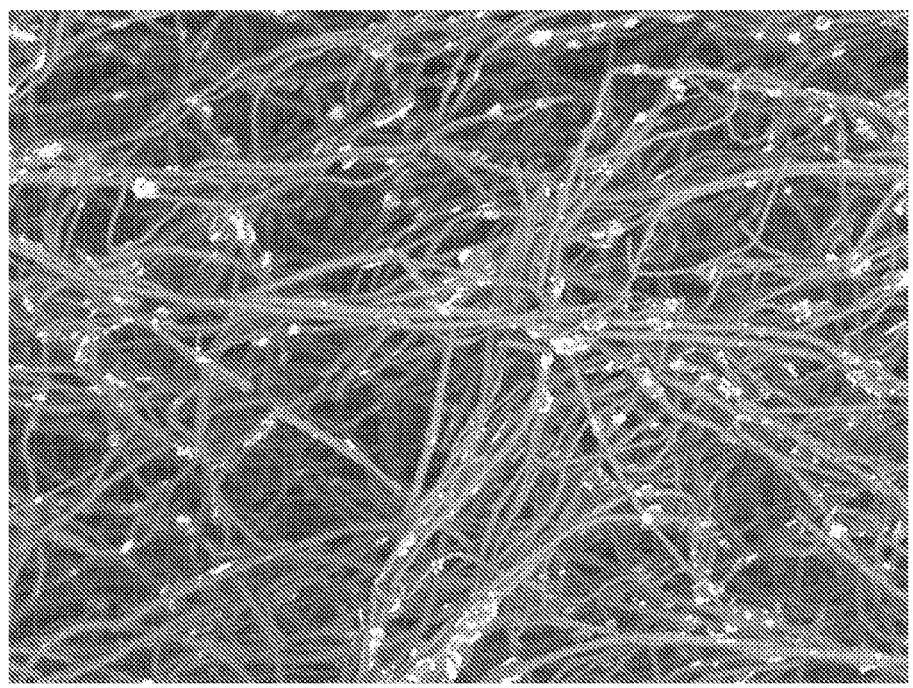
FIG. 21 is an SEM of the rotational spun coating of FIG. 20 at 950× magnification.

FIG. 20 is an SEM of the PTFE/PEO/bismuth subcarbonate mat at a magnification of 170×, and FIG. 21 is an SEM of the same PTFE/PEO/bismuth subcarbonate mat at a magnification of 950×.

Example 16

The degree of endothelial cell attachment (ECA) to the PTFE/PEO mat with a bismuth/FEP midlayer or stripe (Bi/FEP Stripe), as described in Example 14 and shown in FIG. 19, was determined using an endothelial cell attachment assay. The PTFE/PEO with Bi/FEP Stripe material was tested to determine its ability to support the attachment of porcine aortic endothelial cells.

A standard curve with a range of endothelial cell seeding densities was generated to correlate with the PTFE/PEO with Bi/FEP Stripe material. In addition to the rotational spun samples, a number of expanded PTFE (ePTFE) material samples were also tested to provide a reference or comparison for the rotational spun materials. The ePTFE material used was the commercially available Bard Impra Straight Thinwall Vascular Graft (Cat #80S06TW), which is often used as a control material in relevant literature as it is known to have a favorable biological response and favorable endothelial cell attachment.

The PTFE/PEO with Bi/FEP Stripe materials were assembled into a Beem capsule assembly, then ETO sterilized. Beem assemblies were pre-wetted with 200 µl of D-PBS at 37° C. in 5% $CO_2$ for 30 minutes. Triplicate Beem assemblies were seeded with 50K endothelial cells, with the exception of a Beem control (media only). An endothelial cell standard curve was prepared in a 96 well plate with duplicate wells for 0, 1.25K, 2.5K, 5K, 10K, 20K, 40K and 60K endothelial cells per well. Endothelial cells were allowed to attach 90 minutes at 37° C. in 5% $CO_2$.

At 90 minutes, non-attached cells were removed from the Beem assemblies by pipetting off media, gently rinsing with 200 µl D-PBS, then adding 200 µl fresh media. 50 µl of XTT stock solution (1 mg/ml XTT (2,3-bis-(2-methoxy-4-nitro-5-sulfophenyl)-2H-tetrazolium-5-carboxanilide) and 32 µM PMS (5-methylphenazinium methyl sulfate) were added to each Beem assembly and all wells of the standard curve and incubated at 37° C. in 5% $CO_2$ for 3 hours. The wells for the standard curve were not rinsed.

At 3 hours, the media/XTT solution was mixed, then 150 μl was transferred to clean wells in a 96 well plate. Actively respiring cells convert the water-soluble XTT, in the presence of intermediate electron acceptor PMS, to a water-soluble, orange formazan product. Thus, after the incubation period, formazan is in solution in the media in each well. Absorbance was measured at 450 nm with a 650 nm reference.

Figure 22:
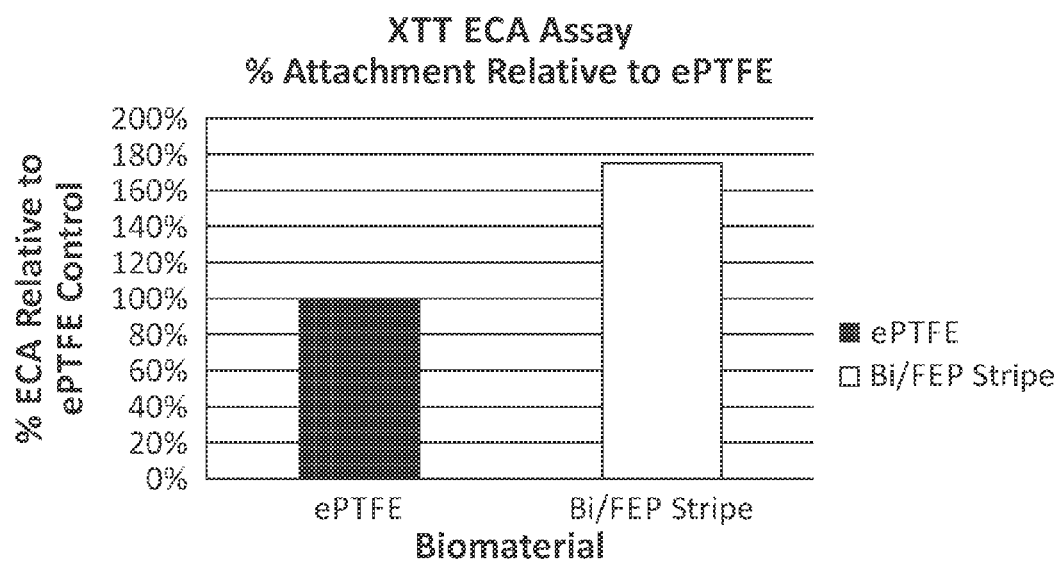
FIG. 22 is a graph showing the results of an endothelial cell assay (ECA).

As shown in FIG. 22, the optical density (OD) of each well was read at 450 nm and at 650 nm. The background absorbance at 650 nm was subtracted from the 450 nm absorbance and the results were graphed. As used herein, "optical density" measures the absorbance of light in the solution. In this example, the greater the number of cells which attach to the material, and are available to react with the XTT/PMS, the darker the color of the supernatant (due to an increased amount of formazan) and, therefore, the higher the optical density (or absorbance of light) of the sample. Assuming that all the cells in the experiment convert XTT to its formazan derivative at the same rate, the optical density measurement is directly proportional to the number of attached cells.

The percent endothelial cell attachment was greater than 170% (n=5) for the PTFE/PEO with Bi/FEP Stripe mats compared to the ePTFE controls, showing that the presence of bismuth in the rotational spun coating increases endothelial cell attachment.

The materials disclosed herein may be configured to achieve various amounts of endothelial cell attachment as defined by this assay. As described herein, the addition of bismuth to the mat, changes to the percent porosity of a mat, the thickness of the mat, and/or the diameter of fibers comprising the mat may influence the characteristics of the mat, including the response of the material to this assay.

Exemplary Embodiments

The following embodiments are illustrative and exemplary and not meant as a limitation of the scope of the present disclosure in any way.

I. Medical Device

In an embodiment, a medical device comprises a drug-eluting rotational spun coating.

The drug-eluting rotational spun coating may comprise a therapeutic agent selected from at least one of rapamycin, paclitaxel, a bismuth-containing compound, heparin, and analogs thereof.

The drug-eluting rotational spun coating may comprise a therapeutic agent in an amount configured to deliver a pharmaceutically effective dose to a target tissue.

The drug-eluting rotational spun coating may comprise a therapeutic agent in an amount configured to deliver a dose to a target tissue of between about 100 μg and about 600 μg over a desired period of time.

The drug-eluting rotational spun coating may be configured to provide a rapid release of a therapeutic agent to a target tissue.

The drug-eluting rotational spun coating may be configured to provide a rapid release of a therapeutic agent to a target tissue in approximately 5 minutes or less, 4 minutes or less, 3 minutes or less, 2.5 minutes or less, 2 minutes or less, 1.8 minutes or less, 1.6 minutes or less, 1.4 minutes or less, 1.2 minutes or less, 1 minute or less, 0.9 minutes or less, 0.8 minutes or less, 0.7 minutes or less, 0.6 minutes or less, 0.5 minutes or less, 0.4 minutes or less, 0.3 minutes or less, 0.2 minutes or less, and 0.1 minutes or less.

The drug-eluting rotational spun coating may be configured to provide a delayed release of a therapeutic agent to a target tissue.

The drug-eluting rotational spun coating may be configured to provide a delayed release of a therapeutic agent to a target tissue over a time period of at least approximately one day, multiple days, a week, multiple weeks, a month, multiple months, or a year or greater.

The drug-eluting rotational spun coating may comprise at least one of nylon 6-6, polyethylene, polypropylene, PTFE, and Kevlar.

The drug-eluting rotational spun coating may comprise at least one of fibrin, fibrinogen, chitin, chitosan, starch, collagen, hyaluronic acid, alginate, dextran, cellulose, and mixtures thereof.

The drug-eluting rotational spun coating may comprise rotational spun fibers approximately one micron in diameter or smaller.

The drug-eluting rotational spun coating may comprise rotational spun fibers approximately one micron in diameter or greater.

The drug-eluting rotational spun coating may comprise at least two layers of rotational spun fibers, wherein the at least two layers of rotational spun fibers are oriented in approximately the same direction.

The drug-eluting rotational spun coating may comprise at least two layers of rotational spun fibers, wherein the at least two layers of rotational spun fibers are oriented in approximately different directions.

The drug-eluting rotational spun coating may be coupled with a non-spun layer.

The drug-eluting rotational spun coating may comprise rotational spun fibers that cure by sintering.

The drug-eluting rotational spun coating may comprise rotational spun fibers comprising at least one solvent-based material.

The drug-eluting rotational spun coating may comprise rotational spun fibers comprising at least one melt-processable material.

The drug-eluting rotational spun coating may comprise a therapeutic agent that is incorporated before rotational spinning of the drug-eluting rotational spun coating onto the medical device.

The drug-eluting rotational spun coating may comprise a therapeutic agent that is applied after the application of the rotational spun fibers onto the medical device.

The therapeutic agent may be a covalently or ionically bound drug.

The therapeutic agent may be heparin.

The therapeutic agent may be applied to the rotational spun fibers by at least one of spraying, rolling, and brushing.

The drug-eluting rotational spun coating may comprise a therapeutic agent that is mixed with a carrier solution and is then rotational spun onto the medical device, thereby providing rotational spun fibers having attached particles of therapeutic agent.

The therapeutic agent may be bismuth, or a bismuth-containing compound.

The drug-eluting rotational spun coating may comprise a therapeutic agent in powder form that is mixed with a solution and is then rotational spun onto the medical device.

The drug-eluting rotational spun coating may comprise a rotationally spun therapeutic agent.

The drug-eluting rotational spun coating may comprise a rotationally spun bismuth-containing compound.

The drug-eluting rotational spun coating may consist of a rotationally spun therapeutic agent.

The medical device may further comprise an electrospun coating.

The medical device may be a balloon comprising a drug-eluting rotational spun coating.

The medical device may be a stent comprising a drug-eluting rotational spun coating.

The medical device may be a vascular graft comprising a drug-eluting rotational spun coating.

A balloon may comprise a drug-eluting polymer microfiber coating or a drug-eluting polymer nanofiber coating.

A stent may comprise a drug-eluting polymer microfiber coating or a drug-eluting polymer nanofiber coating.

II. Method for Drug Delivery

In an embodiment, a method of delivering a drug to a target tissue using a medical device having a drug-eluting rotational spun coating, comprises: positioning the medical device comprising a drug-eluting rotational spun coating near a target tissue; deploying the medical device, thereby placing the drug-eluting rotational spun coating in contact with the target tissue; and delivering the drug to the target tissue by eluting the drug from the drug-eluting rotational spun coating.

The drug-eluting rotational spun coating may comprise a therapeutic agent selected from at least one of the following: rapamycin, paclitaxel, bismuth, and analogues thereof.

The drug-eluting rotational spun coating may comprise a therapeutic agent in an amount configured to deliver a pharmaceutically effective dose to the target tissue.

The drug-eluting rotational spun coating may be configured to provide a rapid release of a therapeutic agent to a target tissue.

The drug-eluting rotational spun coating may be configured to provide a rapid release of a therapeutic agent to a target tissue in approximately 5 minutes or less, 4 minutes or less, 3 minutes or less, 2.5 minutes or less, 2 minutes or less, 1.8 minutes or less, 1.6 minutes or less, 1.4 minutes or less, 1.2 minutes or less, 1 minute or less, 0.9 minutes or less, 0.8 minutes or less, 0.7 minutes or less, 0.6 minutes or less, 0.5 minutes or less, 0.4 minutes or less, 0.3 minutes or less, 0.2 minutes or less, and 0.1 minutes or less.

The drug-eluting rotational spun coating may be configured to provide a delayed release of a therapeutic agent to a target tissue.

The drug-eluting rotational spun coating may be configured to provide a delayed release of a therapeutic agent to a target tissue over a time period of at least approximately one day, multiple days, a week, multiple weeks, a month, multiple months, or a year or greater.

The drug-eluting rotational spun coating may comprise at least one of nylon 6-6, polyethylene, polypropylene, PTFE, and Kevlar.

The drug-eluting rotational spun coating may comprise at least one of the following: fibrin, fibrinogen, chitin, chitosan, starch, collagen, hyaluronic acid, alginate, dextran, cellulose, and mixtures thereof.

The drug-eluting rotational spun coating may comprise rotational spun fibers approximately one micron in diameter or smaller.

The drug-eluting rotational spun coating may comprise rotational spun fibers approximately one micron in diameter or greater.

The drug-eluting rotational spun coating may comprise at least two layers of rotational spun fibers, wherein the at least two layers of rotational spun fibers are oriented in approximately the same direction.

The drug-eluting rotational spun coating may comprise at least two layers of rotational spun fibers, wherein the at least two layers of rotational spun fibers are oriented in approximately different directions.

The drug-eluting rotational spun coating may be coupled with a non-spun layer.

The drug-eluting rotational spun coating may comprise rotational spun fibers that cure by sintering.

The drug-eluting rotational spun coating may comprise rotational spun fibers comprising at least one solvent-based material.

The drug-eluting rotational spun coating may comprise rotational spun fibers comprising at least one melt-processable material.

The drug-eluting rotational spun coating may comprise a therapeutic agent that is incorporated before rotational spinning of the drug-eluting rotational spun coating onto the medical device.

The drug-eluting rotational spun coating may comprise a therapeutic agent that is applied after the application of the rotational spun fibers onto the medical device.

The therapeutic agent may be applied to the rotational spun fibers by at least on or spraying, rolling, and brushing.

The drug-eluting rotational spun coating may comprise a therapeutic agent that is mixed with a carrier solution and is then rotational spun onto the medical device, thereby providing rotational spun fibers having attached particles of therapeutic agent.

The therapeutic agent may be bismuth, or a bismuth-containing compound.

The drug-eluting rotational spun coating may comprise a rotationally spun therapeutic agent.

The drug-eluting rotational spun coating may comprise a rotationally spun bismuth.

The drug-eluting rotational spun coating may consist of a rotationally spun therapeutic agent.

The medical device may further comprise an electrospun coating.

The medical device may be a balloon comprising a drug-eluting rotational spun coating.

The medical device may be a stent comprising a drug-eluting rotational spun coating.

The medical device may be a vascular graft comprising a drug-eluting rotational spun coating.

While specific embodiments of balloons, catheters, stents, vascular grafts and other medical devices have been illustrated and described, it is to be understood that the disclosure provided is not limited to the precise configuration and components disclosed. Various modifications, changes, and variations apparent to those of skill in the art having the benefit of this disclosure may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the herein-described embodiments without departing from the underlying principles of the disclosure herein.

The invention claimed is:

1. A medical device comprising a drug-eluting rotational spun coating, wherein the drug-eluting rotational spun coating comprises a therapeutic agent in an amount configured to deliver a pharmaceutically effective dose to a target tissue, wherein the drug-eluting rotational spun coating is configured to provide a controlled release of the therapeutic agent to the target issue in approximately 5 minutes or less, wherein the drug-eluting rotational spun coating comprises at least two layers of rotational spun fibers having a diameter of between about 50 nanometers and about 3 micrometers, and wherein the drug-eluting rotational spun coating has a percent porosity of between about 30% and about 80%.

2. The medical device of claim 1, wherein the therapeutic agent is selected from at least one of rapamycin, paclitaxel, a bismuth-containing compound, heparin, and analogs of any of the foregoing.

3. The medical device of claim 1, wherein the rotational spun coating is configured to deliver a dose of a therapeutic agent to a target tissue of between about 100 μg and about 600 μg.

4. The medical device of claim 1, wherein the drug-eluting rotational spun coating comprises at least one of nylon 6-6, polyethylene, polypropylene, PTFE, and Kevlar.

5. The medical device of claim 1, wherein the drug-eluting rotational spun coating comprises at least one of fibrin, fibrinogen, chitin, chitosan, starch, collagen, hyaluronic acid, alginate, dextran, cellulose, and mixtures thereof.

6. The medical device of claim 1, wherein the drug-eluting rotational spun coating comprises rotational spun fibers between 750 nanometers and 2 microns in diameter.

7. The medical device of claim 1, wherein the drug-eluting rotational spun coating comprises a percent porosity of between about 40% and about 60%.

8. The medical device of claim 1, wherein the drug-eluting rotational spun coating comprises at least one layer of a drug-eluting rotational spun material, and at least one layer of a non-drug-eluting rotational spun material.

9. The medical device of claim 1, further comprising at least one layer of a non-spun material.

10. The medical device of claim 1, wherein the therapeutic agent is associated with the drug-eluting rotational spun coating via covalent or ionic bonding.

11. The medical device of claim 1, further comprising an electrospun coating.

12. The medical device of claim 1, wherein the medical device is selected from at least one of a balloon, a stent, a catheter or a vascular graft.

13. A medical device comprising a drug-eluting rotational spun coating and at least one layer of non-spun material, wherein the drug-eluting rotational spun coating comprises a therapeutic agent in an amount configured to deliver a pharmaceutically effective dose to a target tissue, wherein the drug-eluting rotational spun coating comprises at least two layers of rotational spun fibers having a diameter of between about 50 nanometers and about 3 micrometers, and wherein the drug-eluting rotational spun coating has a percent porosity of between about 30% and about 80%.

14. The medical device of claim 13, wherein the therapeutic agent is selected from at least one of rapamycin, paclitaxel, a bismuth-containing compound, heparin, and analogs of any of the foregoing.

15. The medical device of claim 13, wherein the rotational spun coating is configured to deliver a dose of a therapeutic agent to a target tissue of between about 100 μg and about 600 μg.

16. The medical device of claim 13, wherein the drug-eluting rotational spun coating is configured to provide a controlled release of a therapeutic agent to a target tissue.

17. The medical device of claim 13, wherein the drug-eluting rotational spun coating comprises at least one of nylon 6-6, polyethylene, polypropylene, PTFE, and Kevlar.

18. The medical device of claim 13, wherein the drug-eluting rotational spun coating comprises at least one of fibrin, fibrinogen, chitin, chitosan, starch, collagen, hyaluronic acid, alginate, dextran, cellulose, and mixtures thereof.

19. The medical device of claim 13, wherein the drug-eluting rotational spun coating comprises rotational spun fibers between 750 nanometers and 2 microns in diameter.

20. The medical device of claim 13, wherein the drug-eluting rotational spun coating comprises a percent porosity of between about 40% and about 60%.

21. The medical device of claim 13, wherein the drug-eluting rotational spun coating comprises at least one layer of a drug-eluting rotational spun material, and at least one layer of a non-drug-eluting rotational spun material.

22. The medical device of claim 13, further comprising an electrospun coating.

23. The medical device of claim 13, wherein the medical device is selected from at least one of a balloon, a stent, a catheter or a vascular graft.

24. A medical device comprising a drug-eluting rotational spun coating, wherein the drug-eluting rotational spun coating comprises a therapeutic agent in an amount configured to deliver a pharmaceutically effective dose to a target tissue, wherein the therapeutic agent is associated with the drug-eluting rotational spun coating via covalent or ionic bonding, wherein the drug-eluting rotational spun coating comprises at least two layers of rotational spun fibers having a diameter of between about 50 nanometers and about 3 micrometers, and wherein the drug-eluting rotational spun coating has a percent porosity of between about 30% and about 80%.

25. The medical device of claim 24, wherein the therapeutic agent is selected from at least one of rapamycin, paclitaxel, a bismuth-containing compound, heparin, and analogs of any of the foregoing.

26. The medical device of claim 24, wherein the rotational spun coating is configured to deliver a dose of a therapeutic agent to a target tissue of between about 100 μg and about 600 μg.

27. The medical device of claim 24, wherein the drug-eluting rotational spun coating comprises at least one of nylon 6-6, polyethylene, polypropylene, PTFE, and Kevlar.

28. The medical device of claim 24, wherein the drug-eluting rotational spun coating comprises at least one of fibrin, fibrinogen, chitin, chitosan, starch, collagen, hyaluronic acid, alginate, dextran, cellulose, and mixtures thereof.

29. The medical device of claim 24, wherein the drug-eluting rotational spun coating comprises rotational spun fibers between 750 nanometers and 2 microns in diameter.

30. The medical device of claim 24, wherein the drug-eluting rotational spun coating comprises a percent porosity of between about 40% and about 60%.

31. The medical device of claim 24, wherein the drug-eluting rotational spun coating comprises at least one layer of a drug-eluting rotational spun material, and at least one layer of a non-drug-eluting rotational spun material.

32. The medical device of claim 24, further comprising an electrospun coating.

33. The medical device of claim 24, wherein the medical device is selected from at least one of a balloon, a stent, a catheter or a vascular graft.

* * * * *